(12) United States Patent
Fletcher et al.

(10) Patent No.: US 8,337,379 B2
(45) Date of Patent: Dec. 25, 2012

(54) BLOOD PROCESSING APPARATUS WITH ROBUST AUTOMATED PROCESS CONTROL

(75) Inventors: Christopher Fletcher, Boulder, CO (US); William Sweat, Lakewood, CO (US); Jeremy Kolenbrander, Brighton, CO (US); Aditya Dalvi, Golden, CO (US); John R. Linder, Morrison, CO (US)

(73) Assignee: Terumo BCT, Inc., Lakewood, CO (US)

( * ) Notice: Subject to any disclaimer, the term of this patent is extended or adjusted under 35 U.S.C. 154(b) by 877 days.

(21) Appl. No.: 11/772,692

(22) Filed: Jul. 2, 2007

(65) Prior Publication Data

US 2008/0045394 A1    Feb. 21, 2008

Related U.S. Application Data

(60) Provisional application No. 60/822,672, filed on Aug. 17, 2006.

(51) Int. Cl.
*B04B 9/10* (2006.01)
*B04B 13/00* (2006.01)
*A61M 37/00* (2006.01)

(52) U.S. Cl. ........... 494/7; 210/94; 210/512.1; 210/782; 356/39; 494/1; 494/10; 494/37; 494/45; 604/6.04

(58) Field of Classification Search .............. 356/39; 494/37, 45; 604/6.04; 210/782
See application file for complete search history.

(56) References Cited

U.S. PATENT DOCUMENTS

| 4,151,844 A | 5/1979 | Cullis et al. |
| 4,493,691 A | 1/1985 | Calari |
| 4,557,719 A | 12/1985 | Neumann et al. |
| 4,670,002 A | 6/1987 | Brown et al. |
| 4,724,317 A | 2/1988 | Brown et al. |
| 4,834,890 A | 5/1989 | Brown et al. |

(Continued)

FOREIGN PATENT DOCUMENTS

DE    3413065 A1    10/1984

(Continued)

OTHER PUBLICATIONS

"Invitation to Pay Additional Fees" with Partial International Search Report; PCT/US2007/072678, Dec. 14, 2007.

(Continued)

*Primary Examiner* — Krishnan S Menon
*Assistant Examiner* — Dirk Bass
(74) *Attorney, Agent, or Firm* — John R. Merkling; Elizabeth J. Reagan; René A. Pereyra

(57) ABSTRACT

A centrifuge for separating blood having a camera observing fluid flow, and a controller controlling the flow. The location of an interface is detected by image processing steps, which may comprise the steps of "spoiling" the image, "diffusing" the image, "edge detection", "edge linking", "region-based confirmation", and "interface calculation". "Spoiling" reduces the number of pixels to be examined preferentially on orthogonal axis oriented with respect to the expected location of the interface or phase boundary. "Diffusing" smoothes out small oscillations in the interface boundary, making the location of the interface more distinct. "Edge detection" computes the rate of change in pixel intensity, or. "Edge linking" connects adjacent maxima. "Region-based confirmation" creates a pseudo image of the regions that qualify as distinct. "Final edge calculation" uses the points where the shade changes in the pseudo image, averages the radial displacement of these points for the interface position.

22 Claims, 33 Drawing Sheets

U.S. PATENT DOCUMENTS

| | | |
|---|---|---|
| 5,076,911 A | 12/1991 | Brown et al. |
| 5,104,526 A | 4/1992 | Brown et al. |
| 5,260,598 A | 11/1993 | Brass et al. |
| 5,316,667 A | 5/1994 | Brown et al. |
| 5,322,620 A | 6/1994 | Brown et al. |
| 5,414,778 A | 5/1995 | Schwartz et al. |
| 5,653,887 A | 8/1997 | Wahl et al. |
| 6,026,174 A | 2/2000 | Palcic et al. |
| 6,053,856 A | 4/2000 | Hlavinka |
| 6,078,680 A | 6/2000 | Yoshida et al. |
| 6,334,842 B1 | 1/2002 | Hlavinka et al. |
| 6,506,606 B1 | 1/2003 | Winkelman et al. |
| 6,514,189 B1 | 2/2003 | Hlavinka et al. |
| 6,707,952 B1 | 3/2004 | Tan et al. |
| 6,790,371 B2 | 9/2004 | Dolecek |
| 2002/0031255 A1 | 3/2002 | Kasdan et al. |
| 2002/0058575 A1 | 5/2002 | Hlavinka et al. |
| 2003/0036751 A1* | 2/2003 | Anderson et al. ............ 606/9 |
| 2004/0153128 A1 | 8/2004 | Suresh et al. |
| 2005/0051466 A1 | 3/2005 | Carter et al. |
| 2007/0085996 A1* | 4/2007 | Mangan et al. ............ 356/39 |

FOREIGN PATENT DOCUMENTS

| | | |
|---|---|---|
| EP | 0392475 A2 | 10/1990 |
| EP | 0392475 A3 | 10/1990 |
| EP | 1146748 | 10/2001 |
| JP | 01216242 | 8/1989 |
| WO | WO99/08091 | 2/1999 |
| WO | WO02/13139 | 2/2002 |
| WO | WO2006/071302 | 7/2006 |

OTHER PUBLICATIONS

Perona et al, Scale-Space and Edge Detection Using Anisotropic Diffusion, *IEEE Transactions on Pattern Analysis and Machine Intelligence*, 1990, v. 12, No. 7, pp. 629-639.

Salgaller, Michael L., A Manifesto on the Current State of Dendritic Cells in Adoptive Immunotherapy, *Transfusion*, 2003, 48:422-424.

* cited by examiner

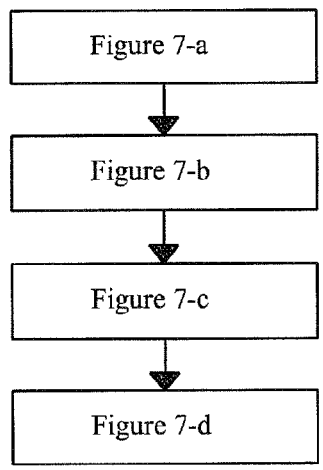
Figure 7
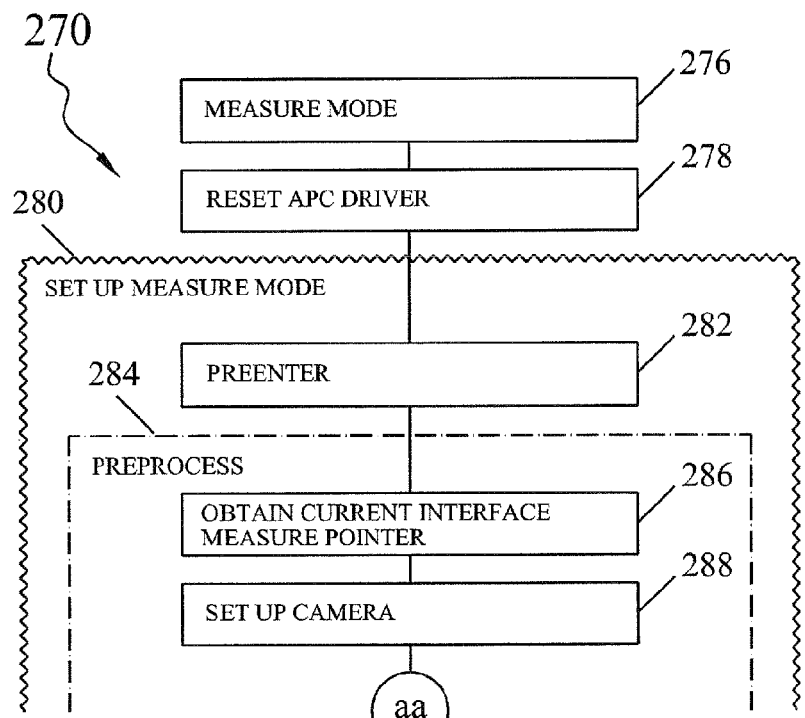
Figure 7-a

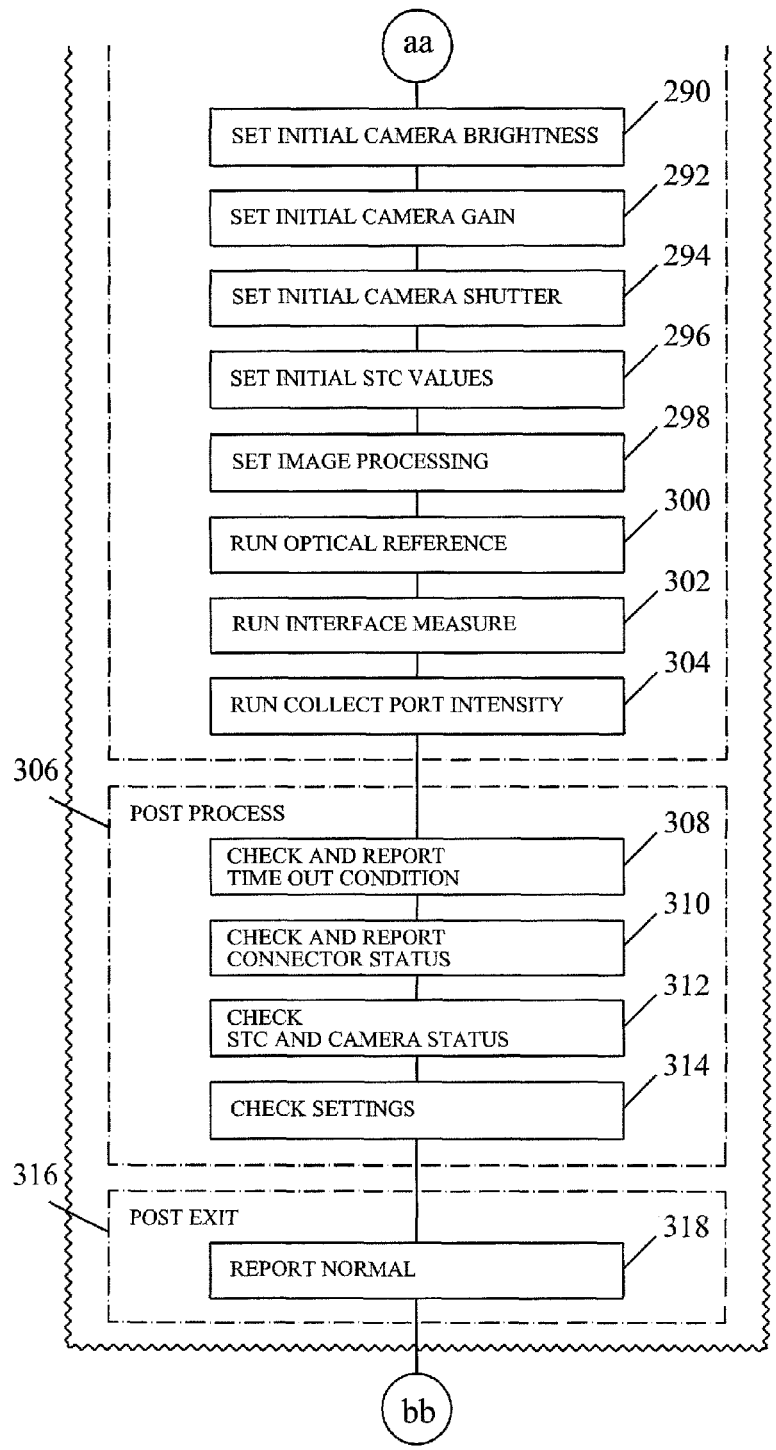
Figure 7-b

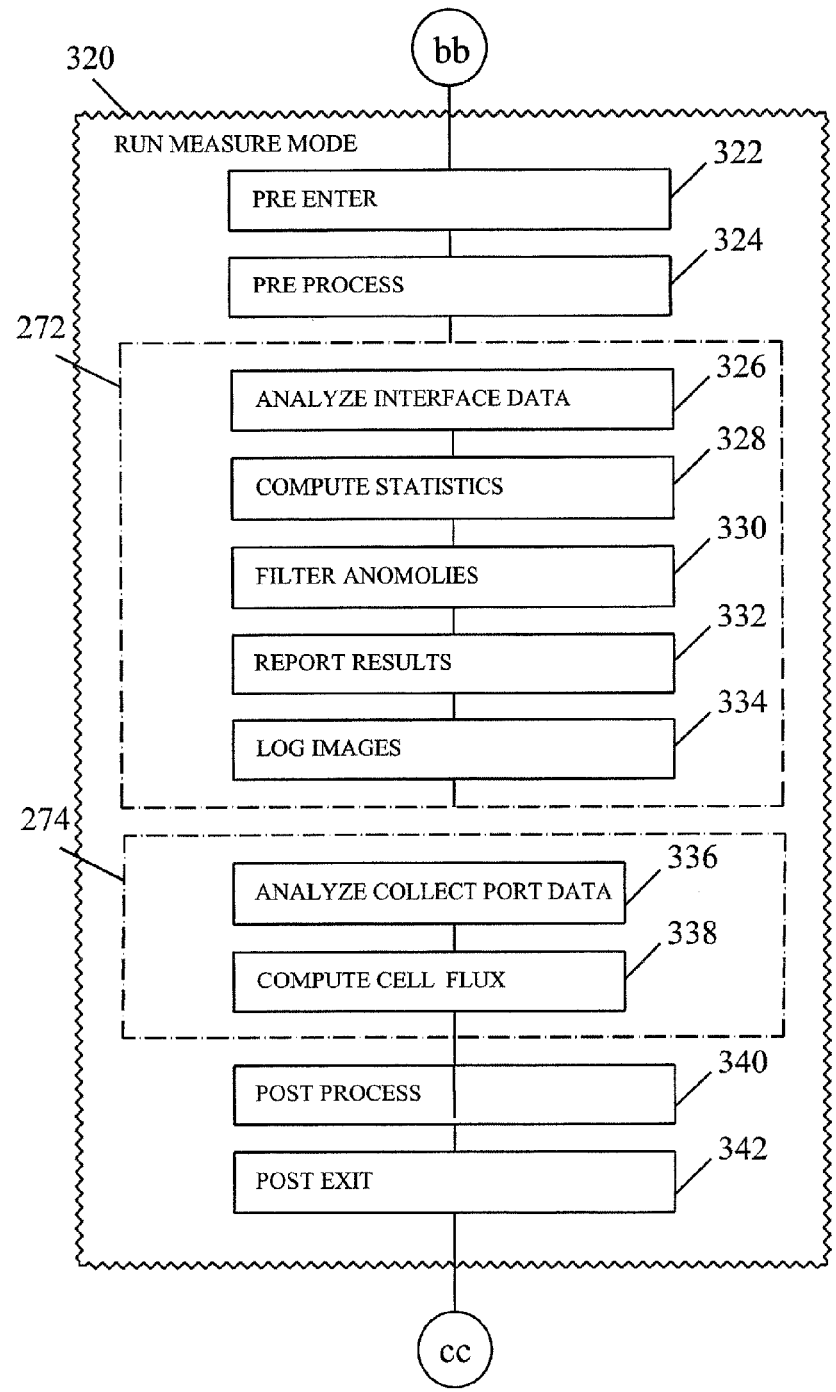
Figure 7-c

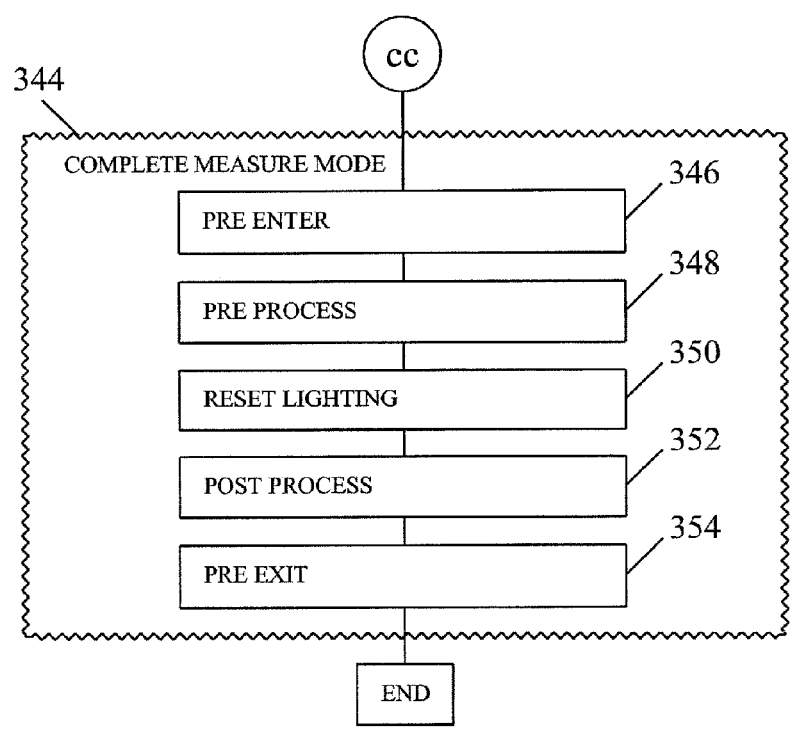
Figure 7-d

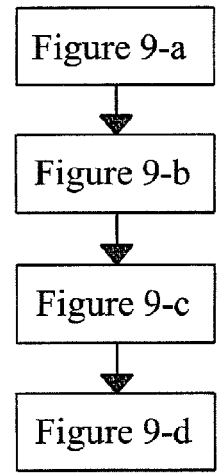
Figure 9
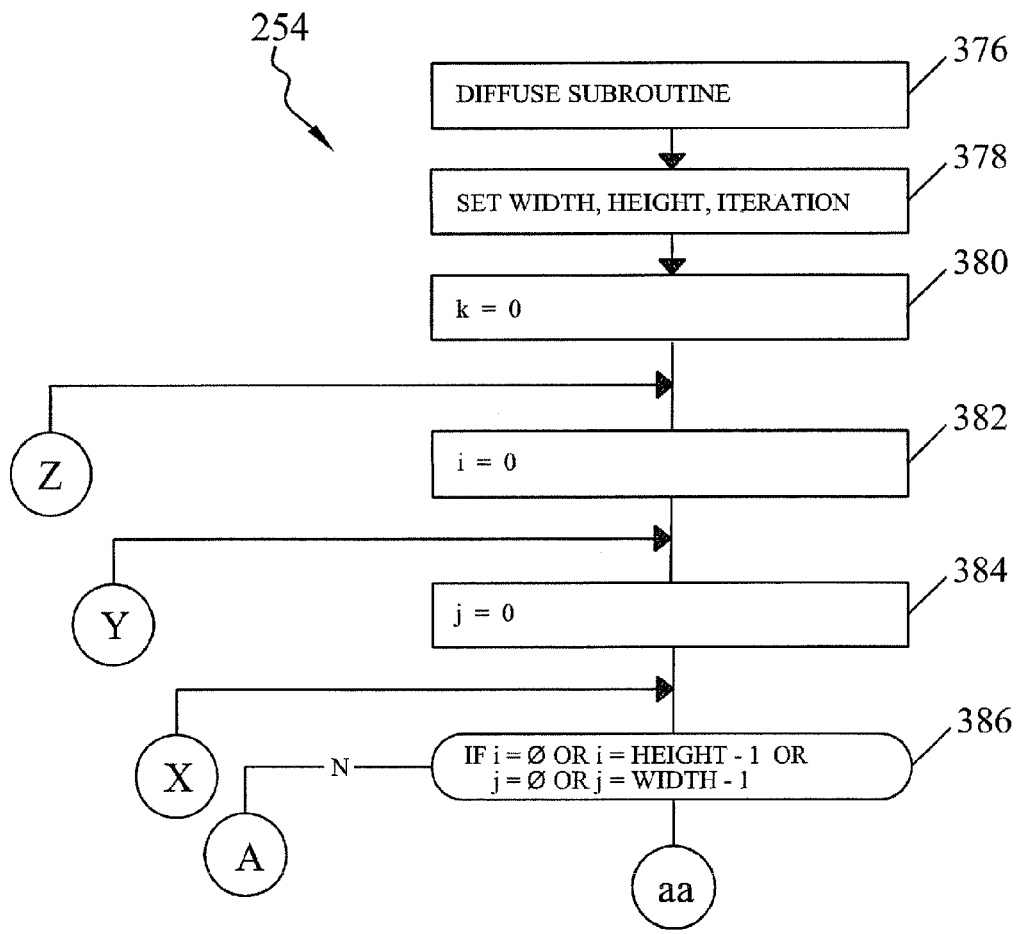
Figure 9-a

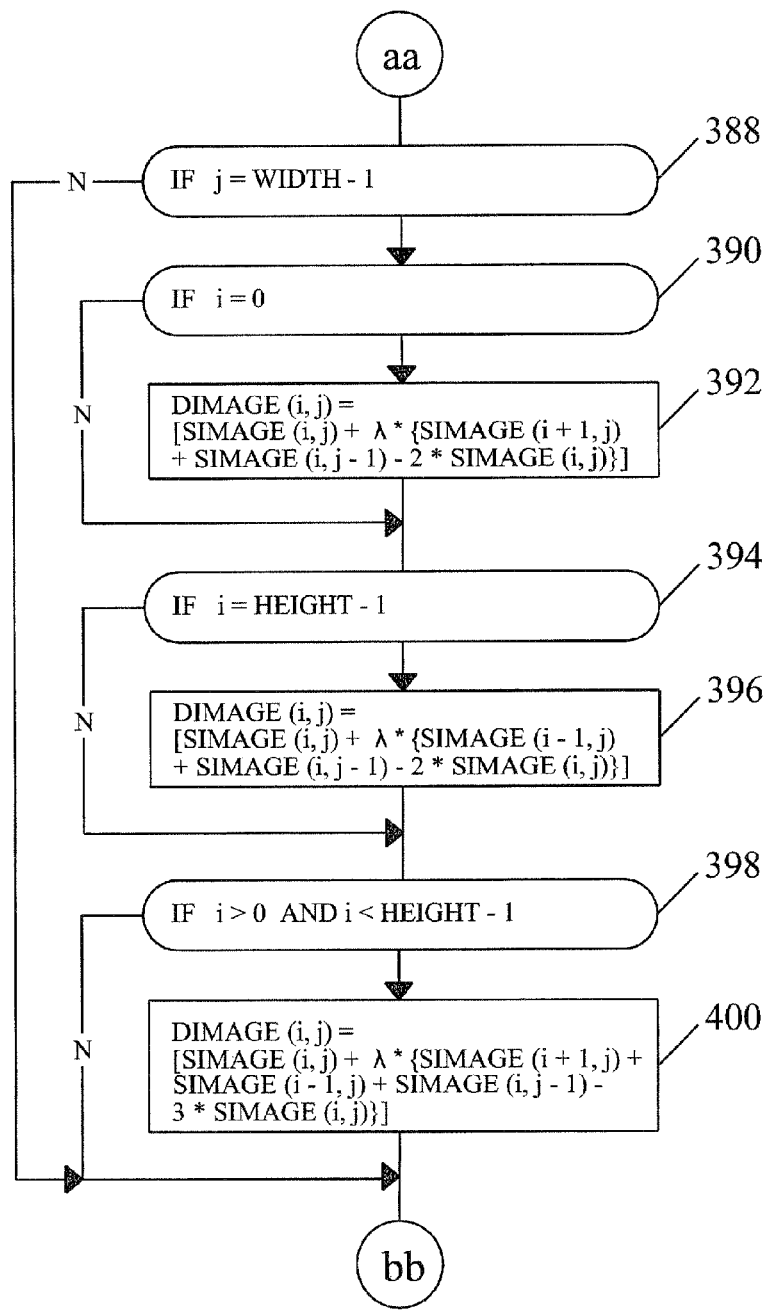
Figure 9-b

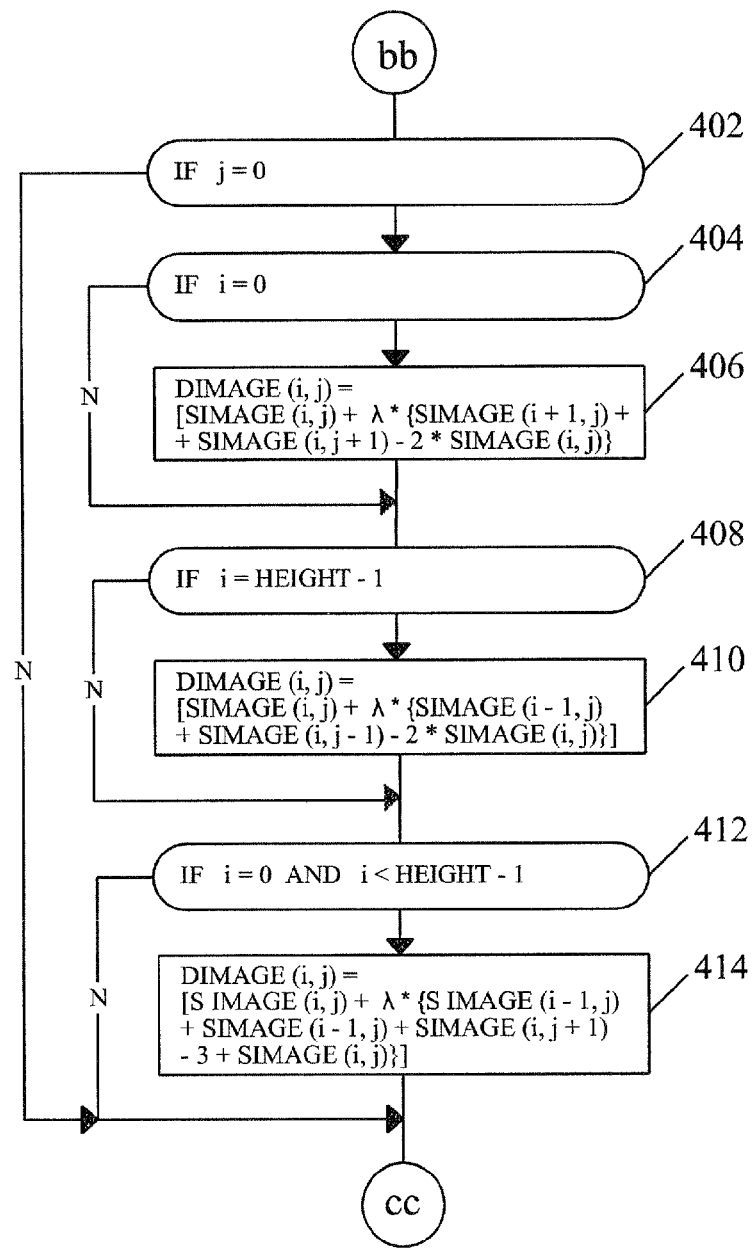
Figure 9-c

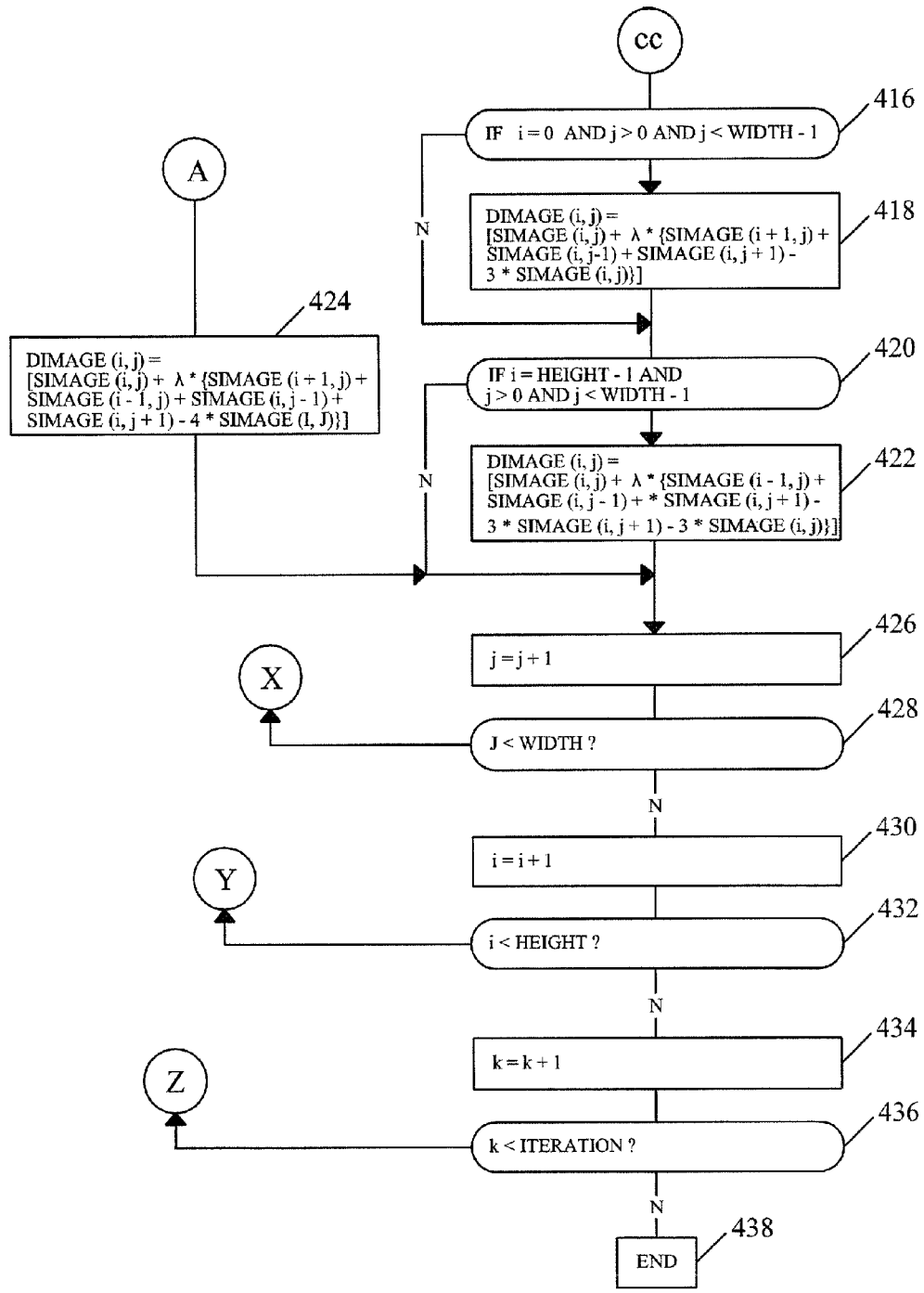
Figure 9-d

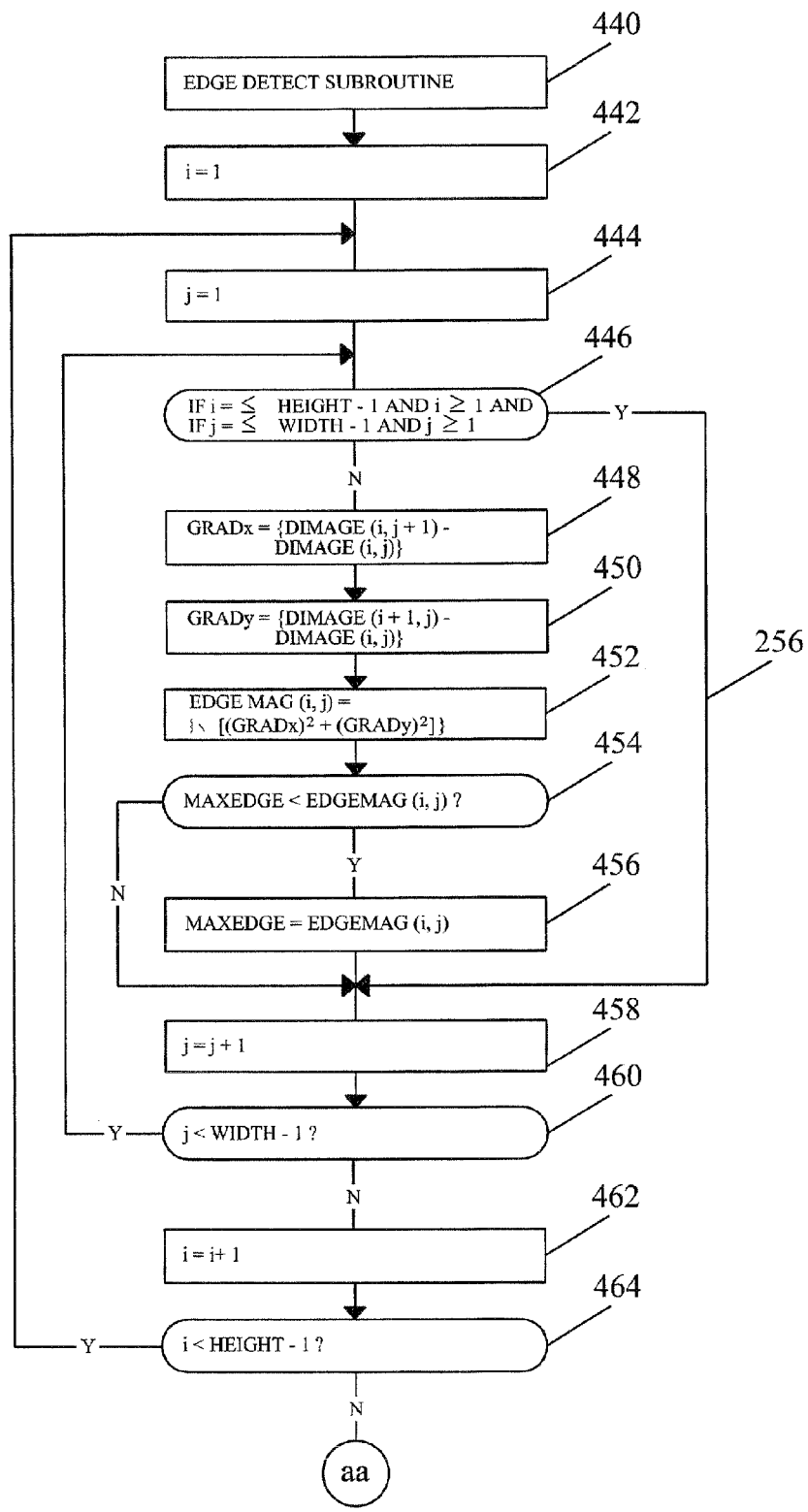
Figure 10-a

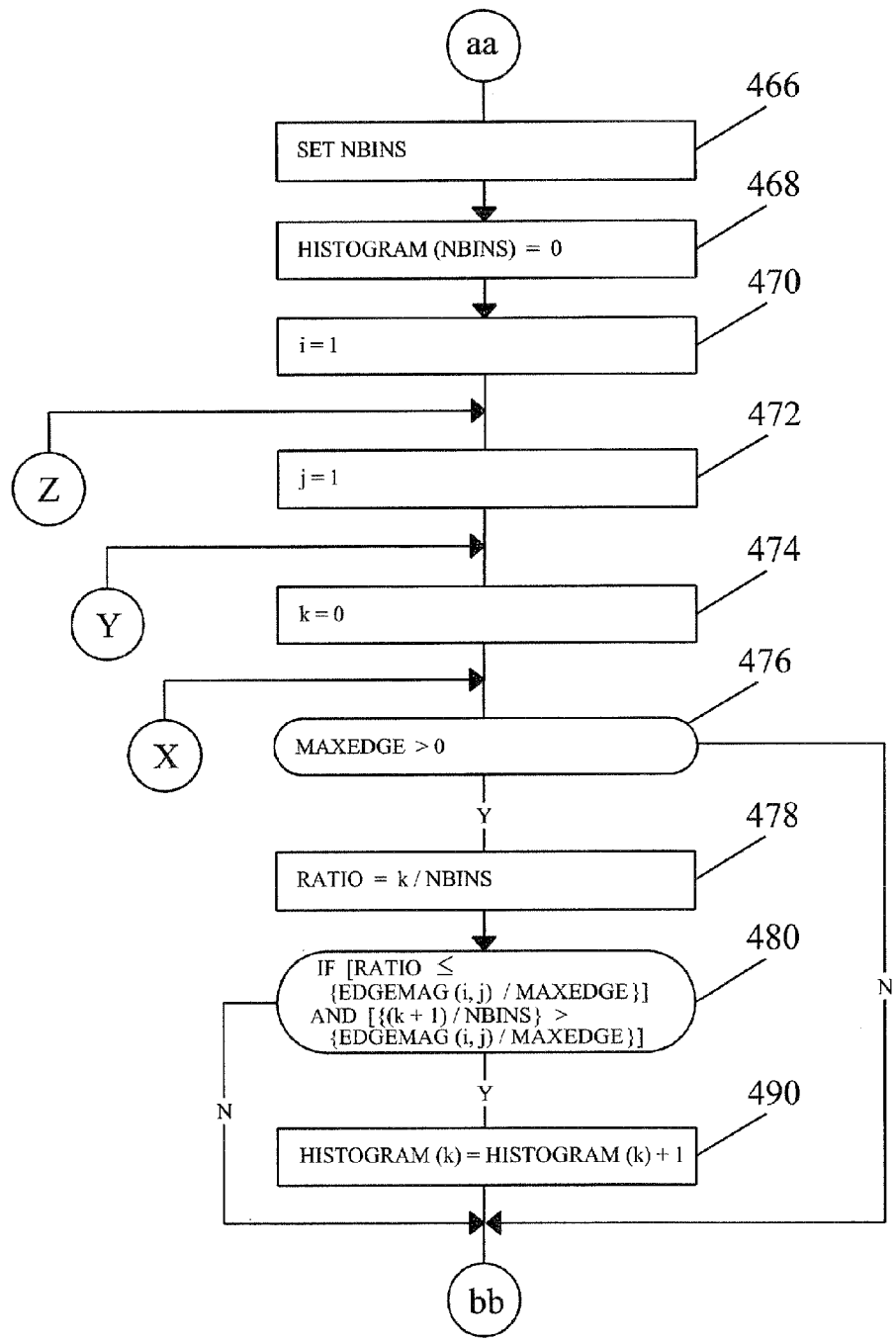
Figure 10-b

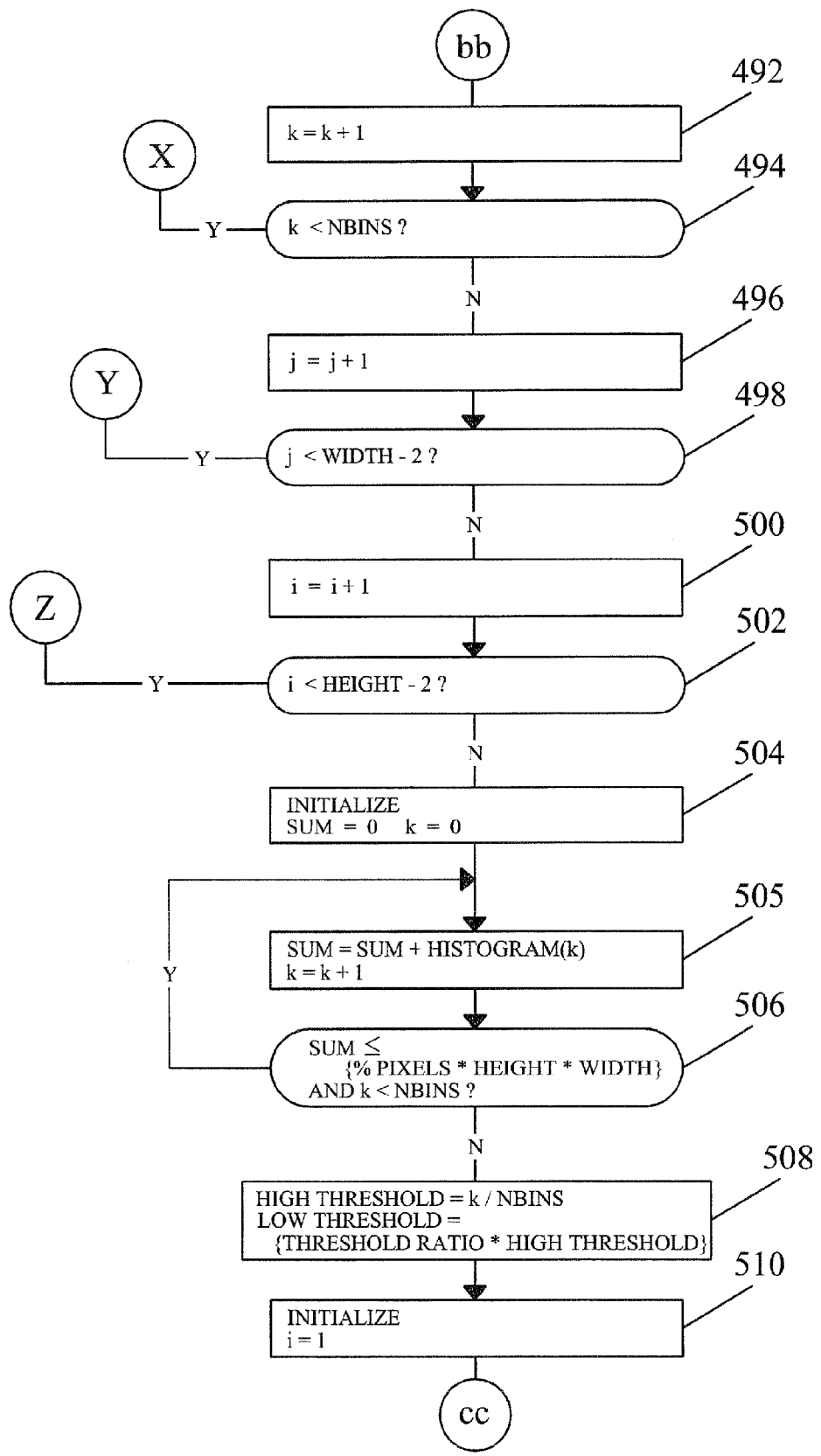
Figure 10-c

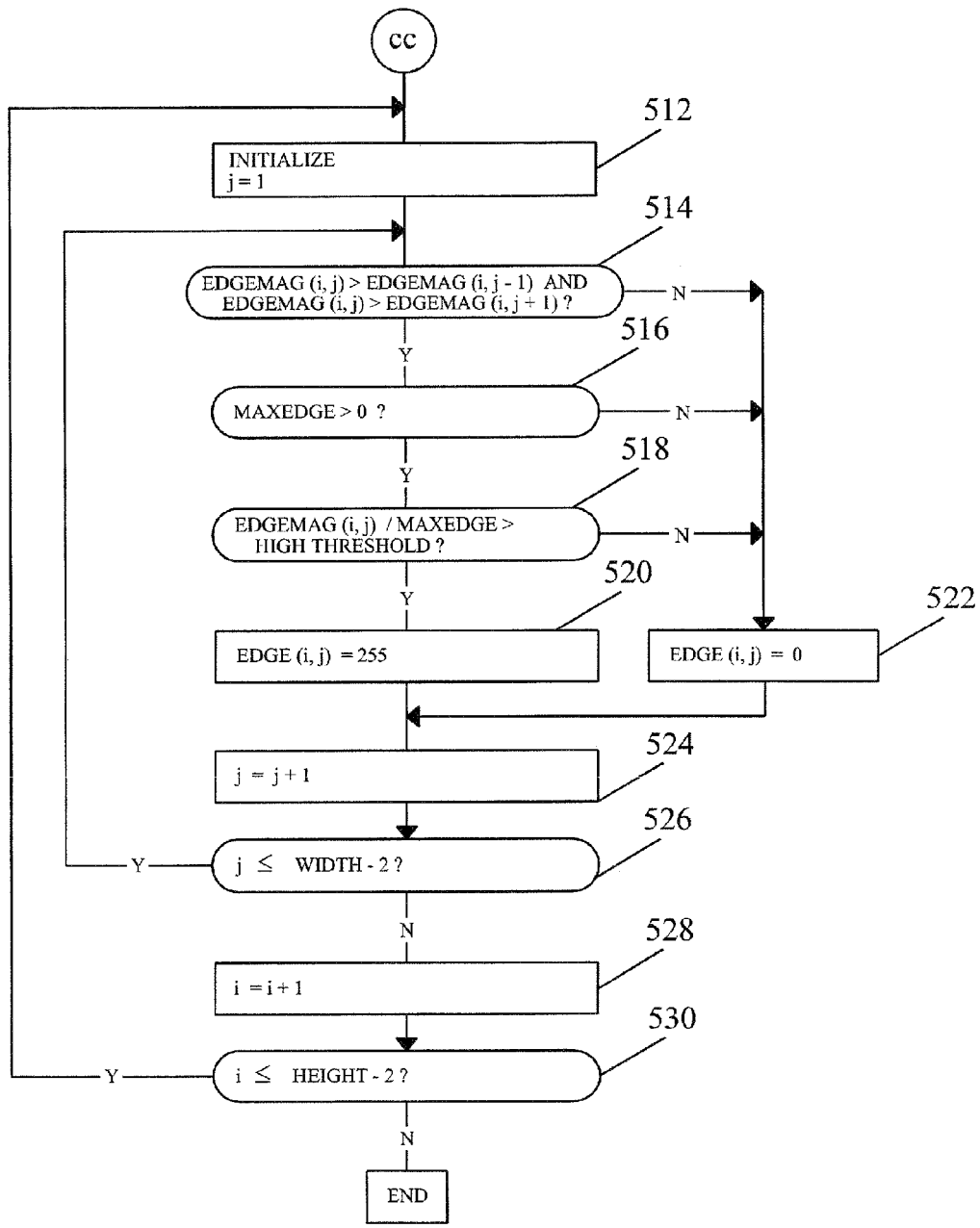
Figure 10-d

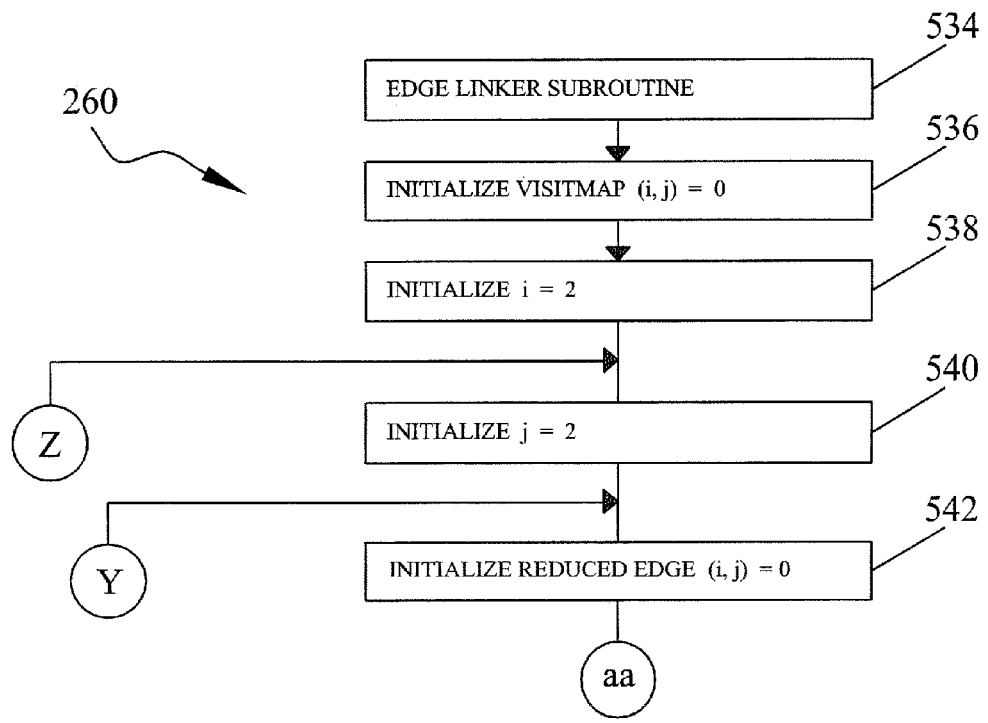
Figure 11
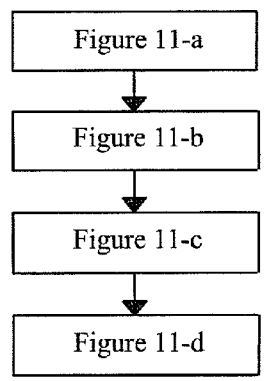
Figure 11-a

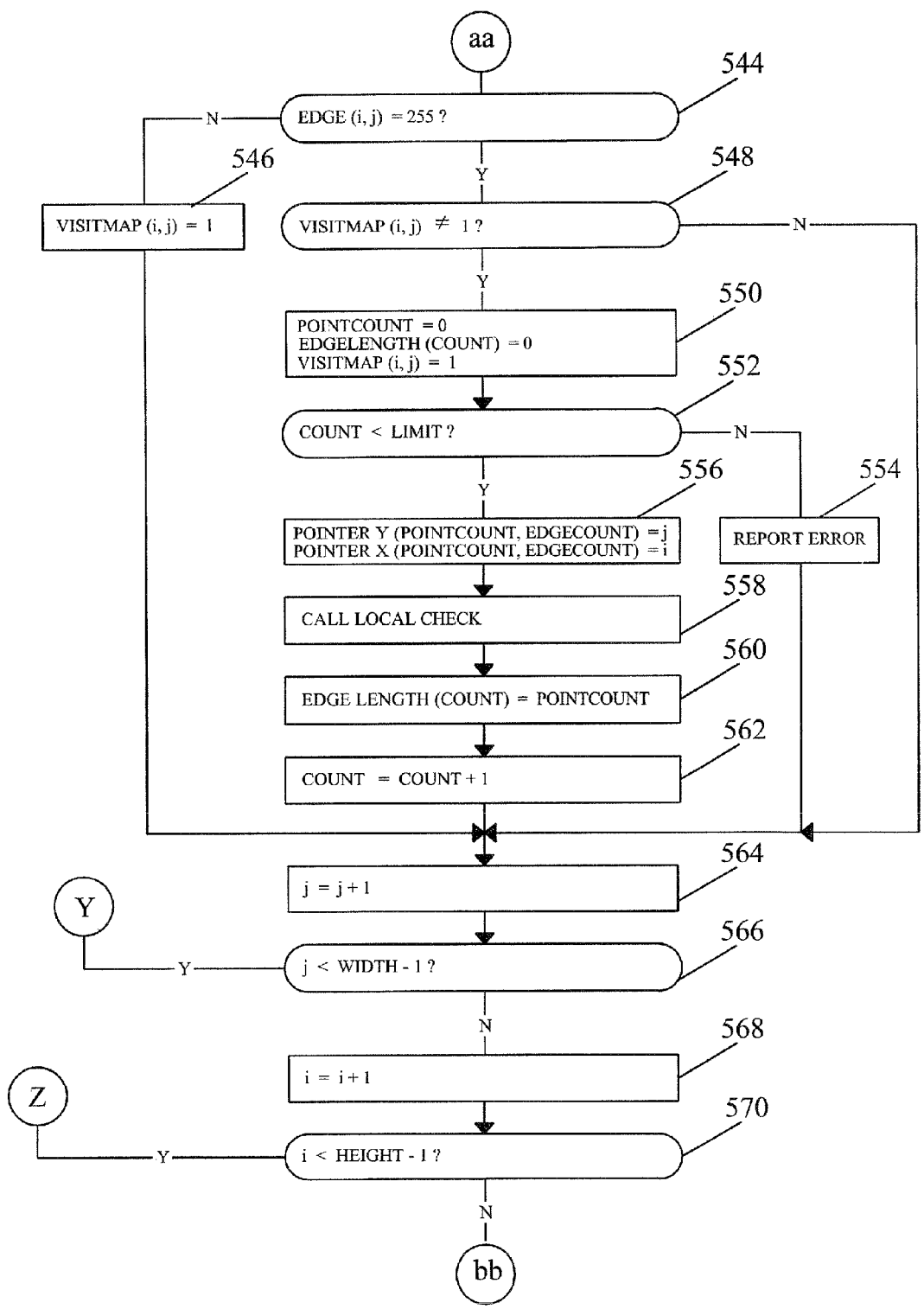
Figure 11-b

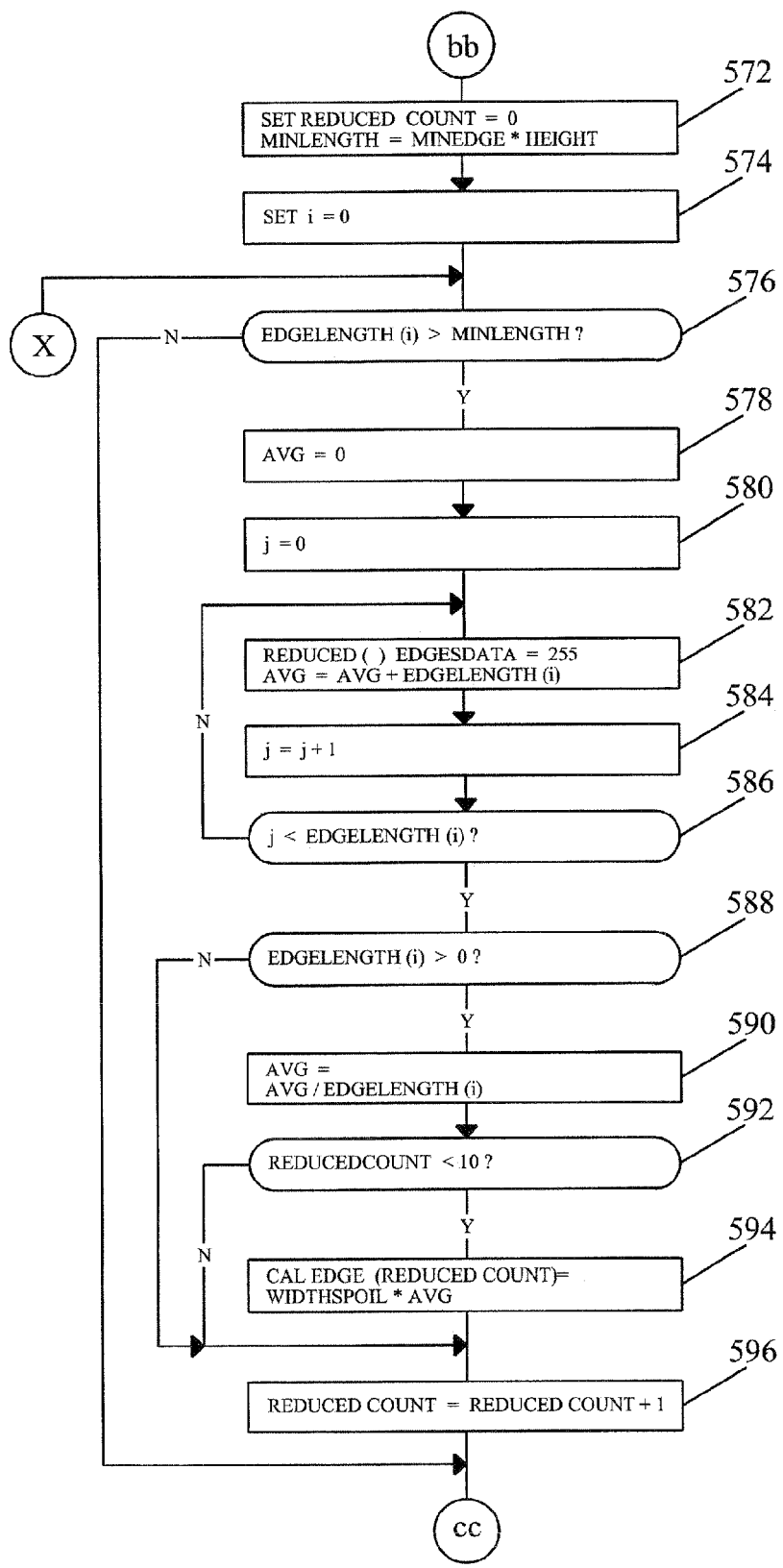
Figure 11-c

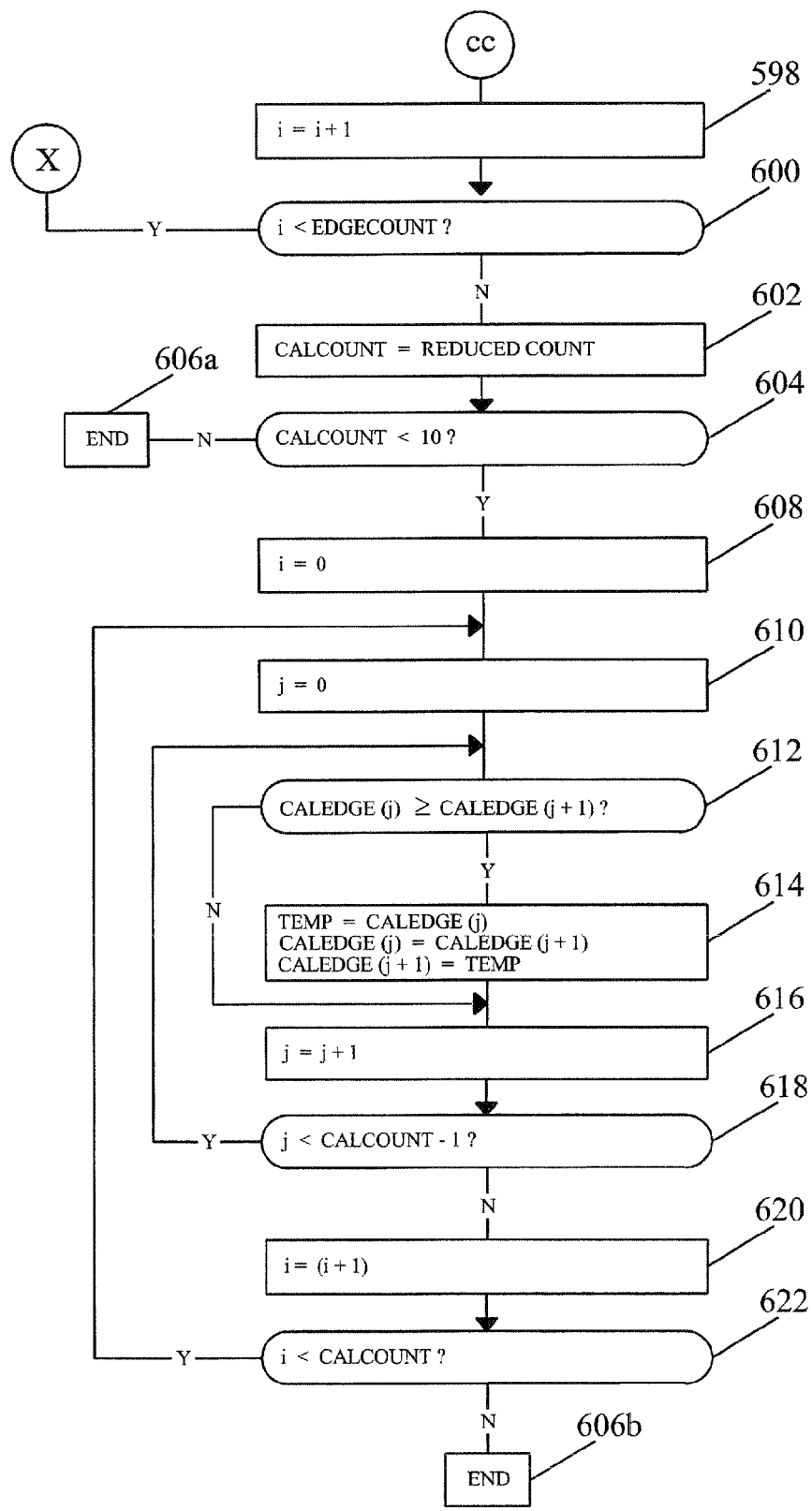
Figure 11-d

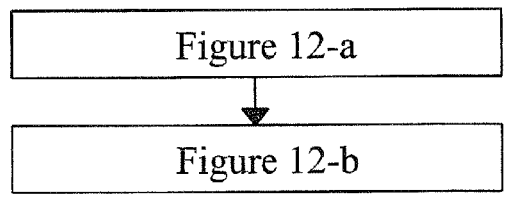
Figure 12
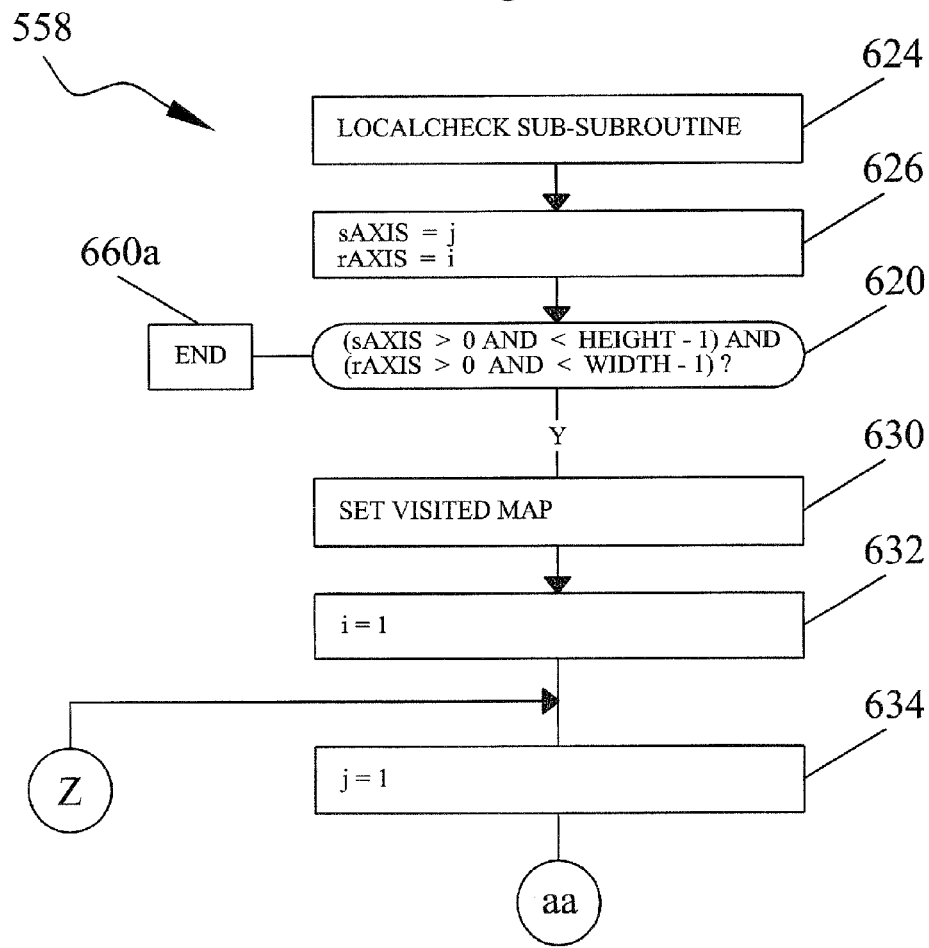
Figure 12-a

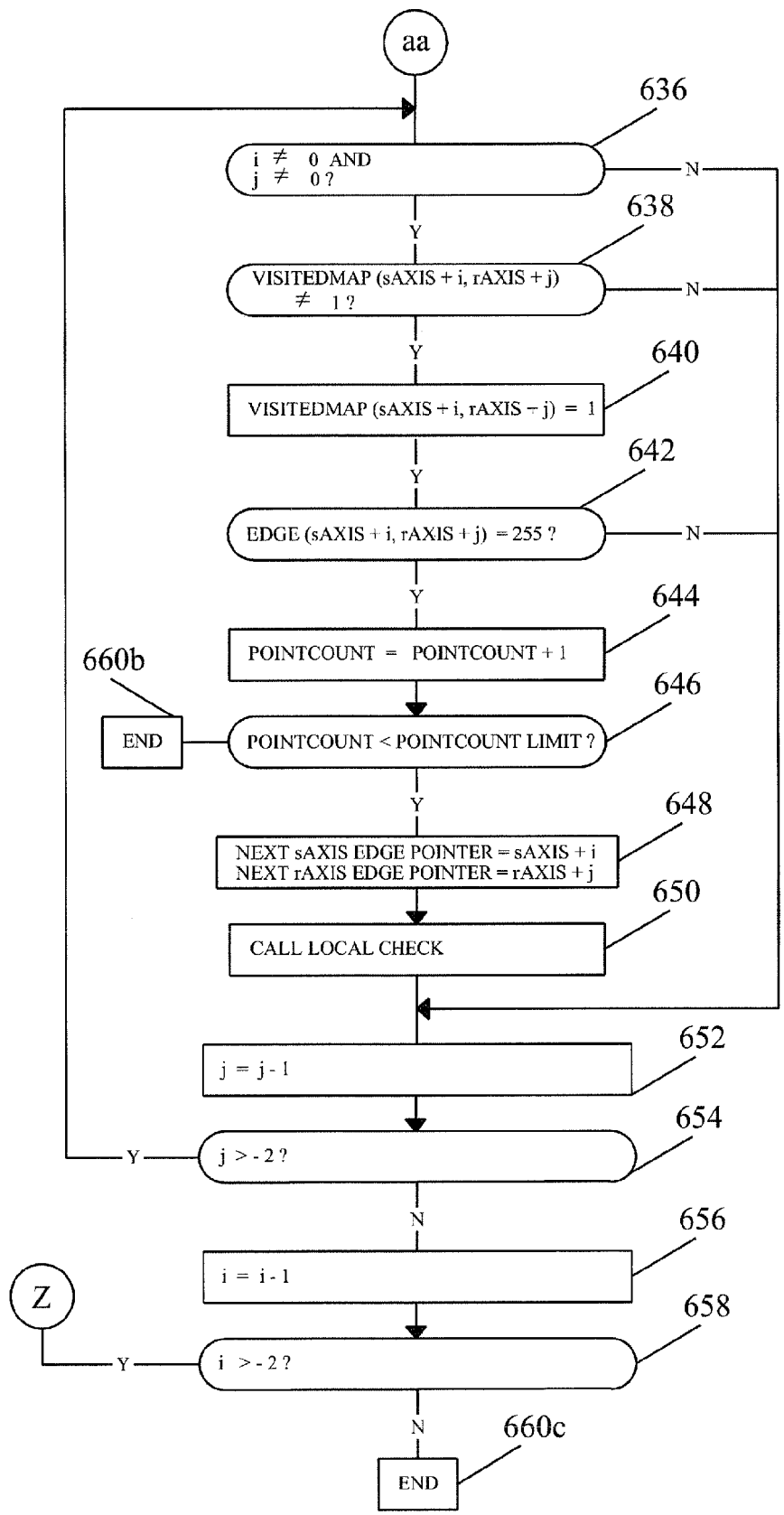
Figure 12-b

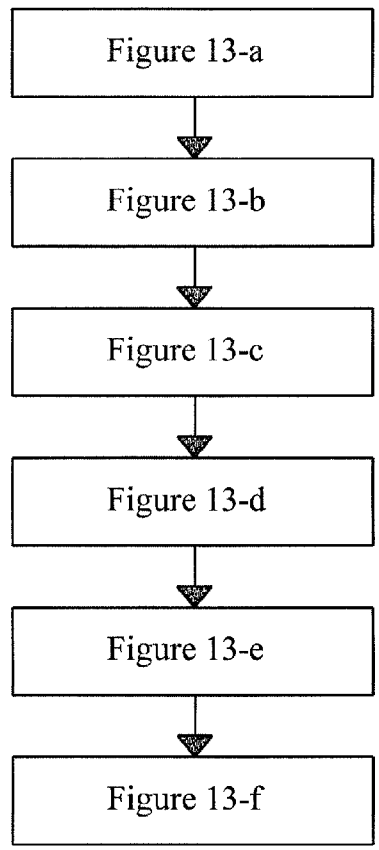
Figure 13
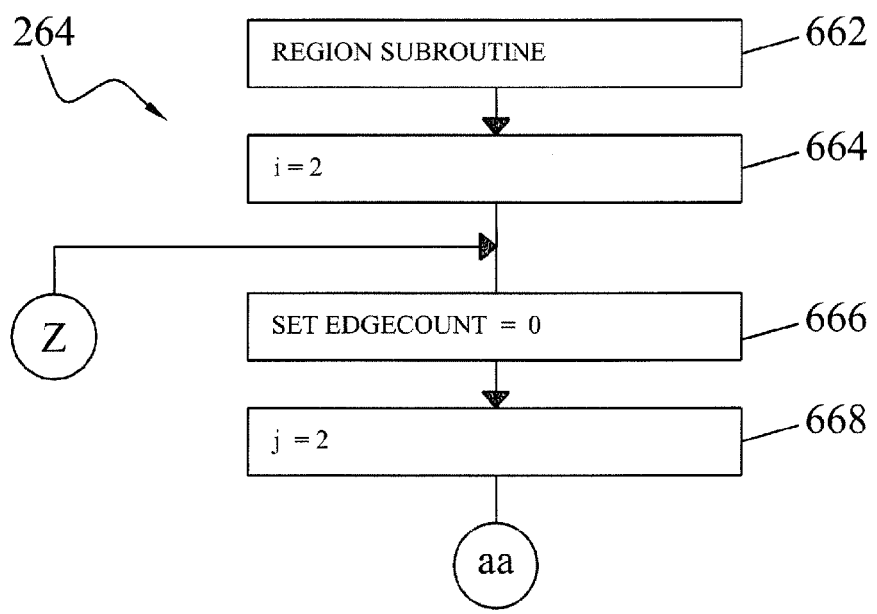
Figure 13-a

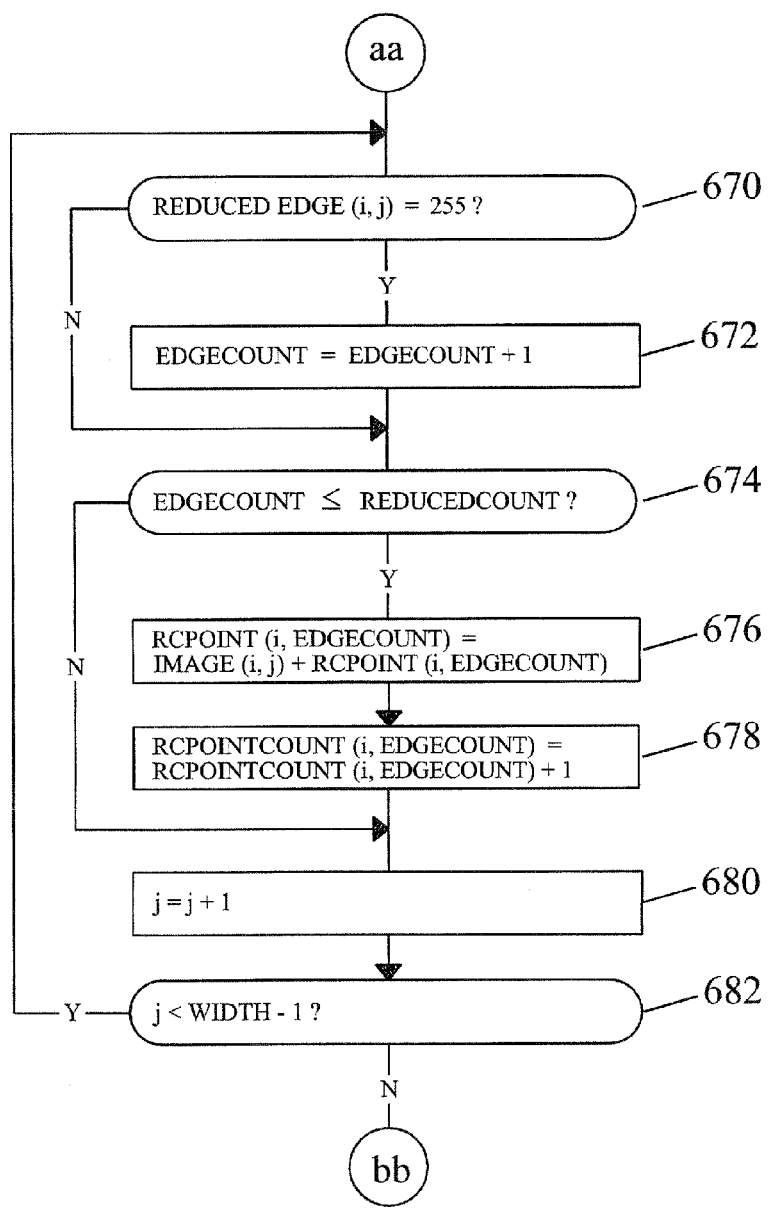
Figure 13-b

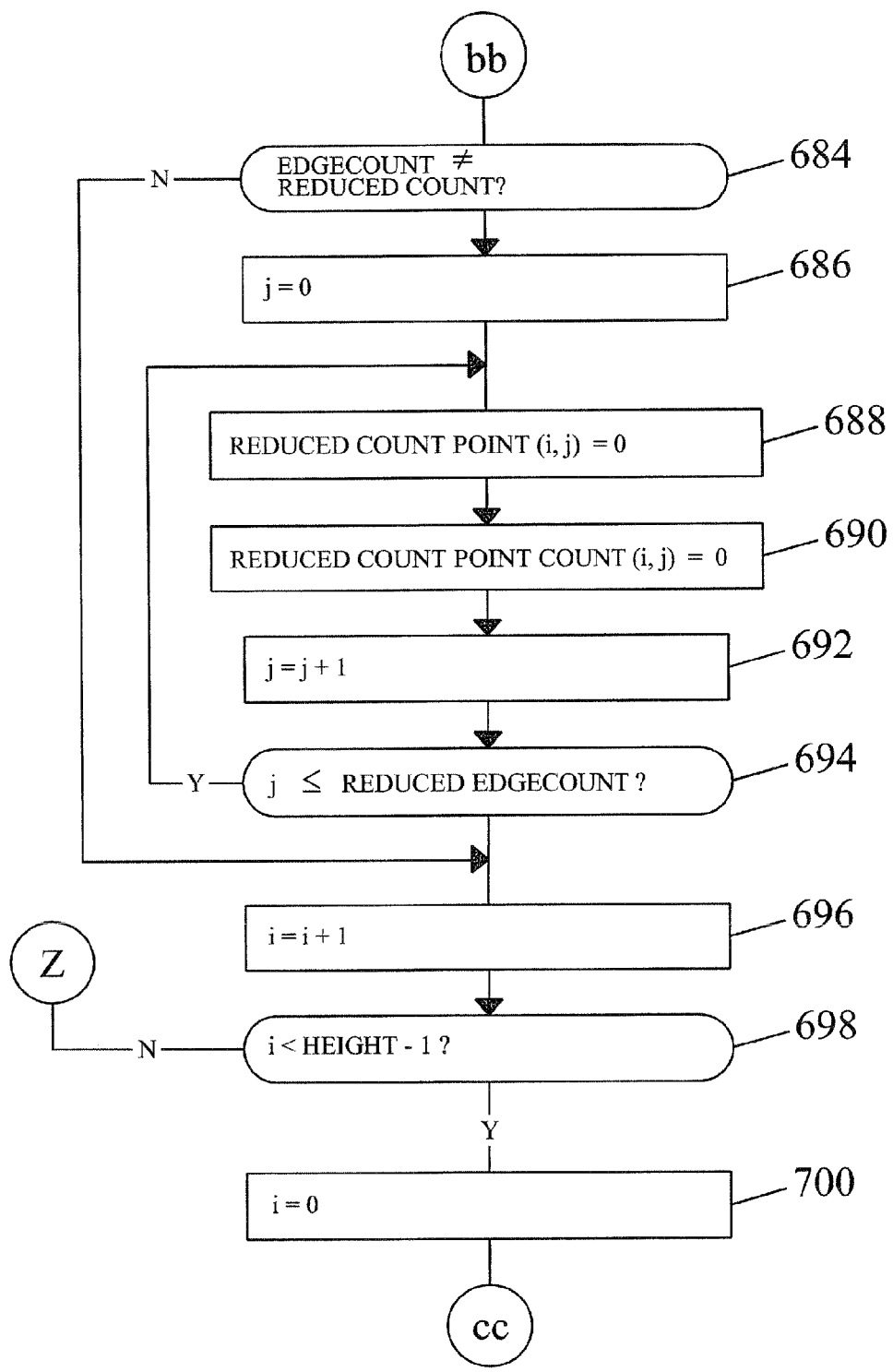
Figure 13-c

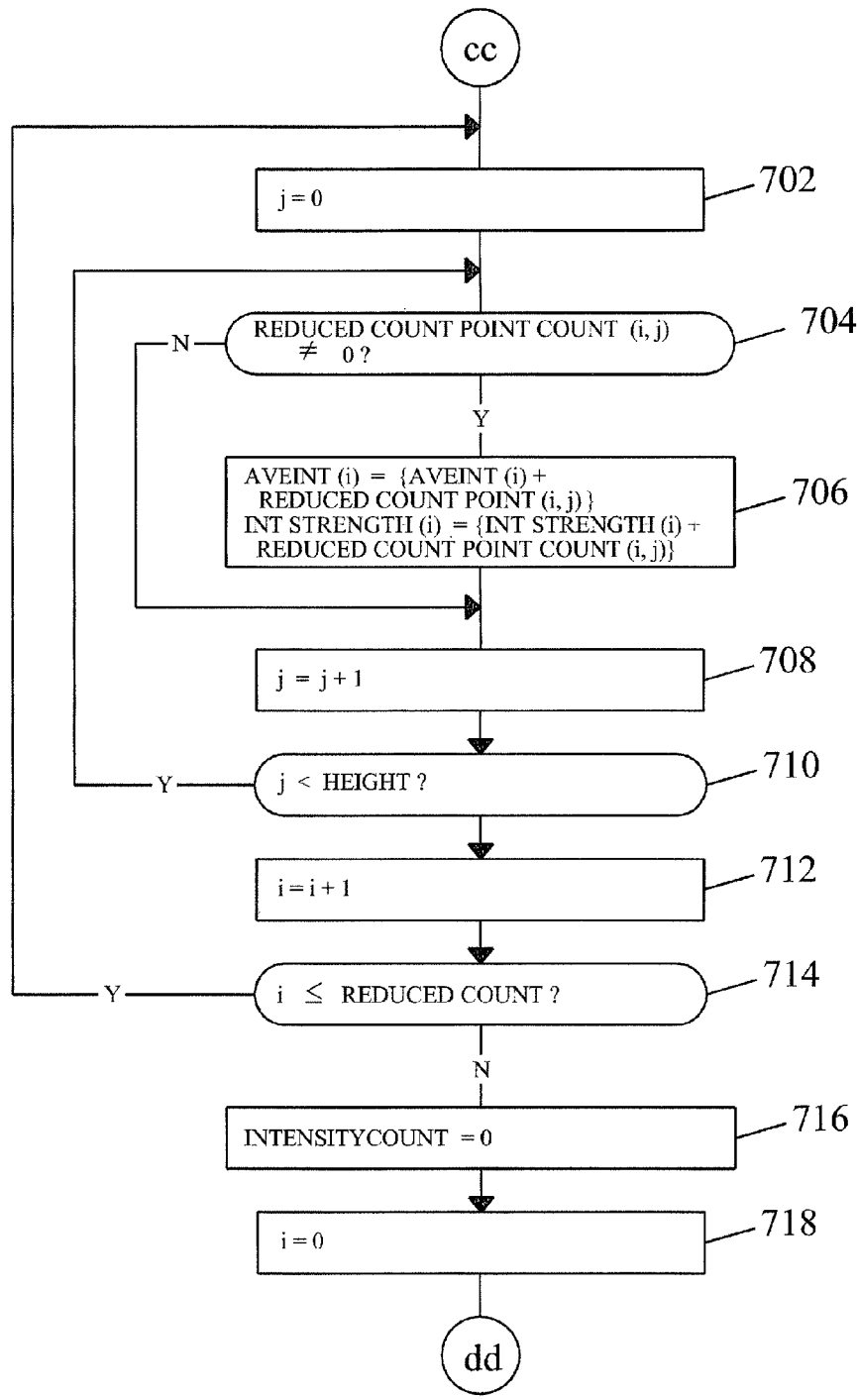
Figure 13-d

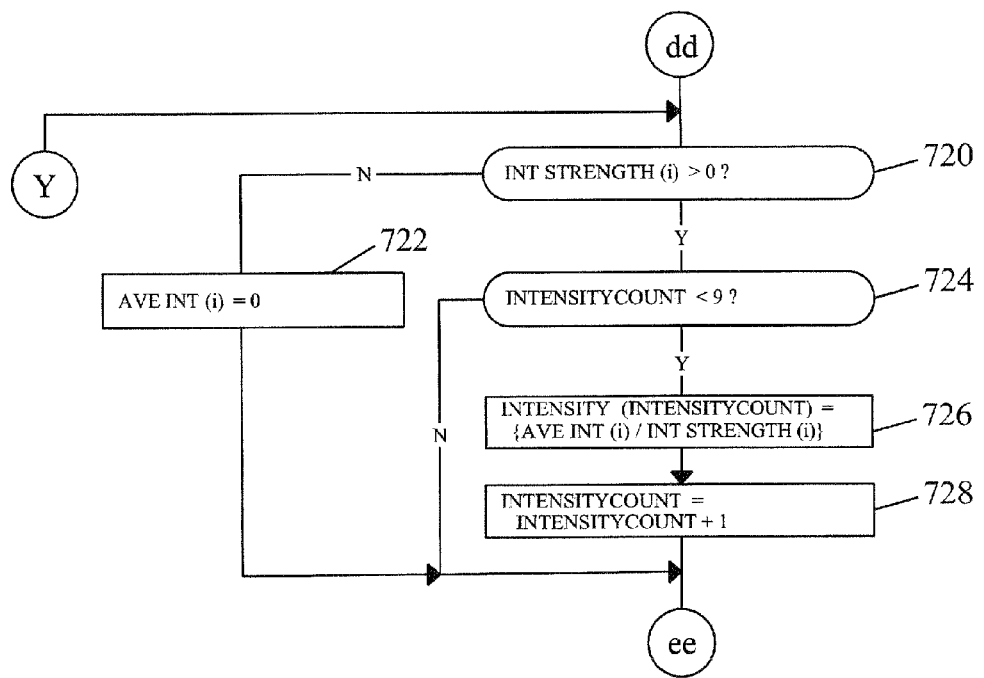
Figure 13-e

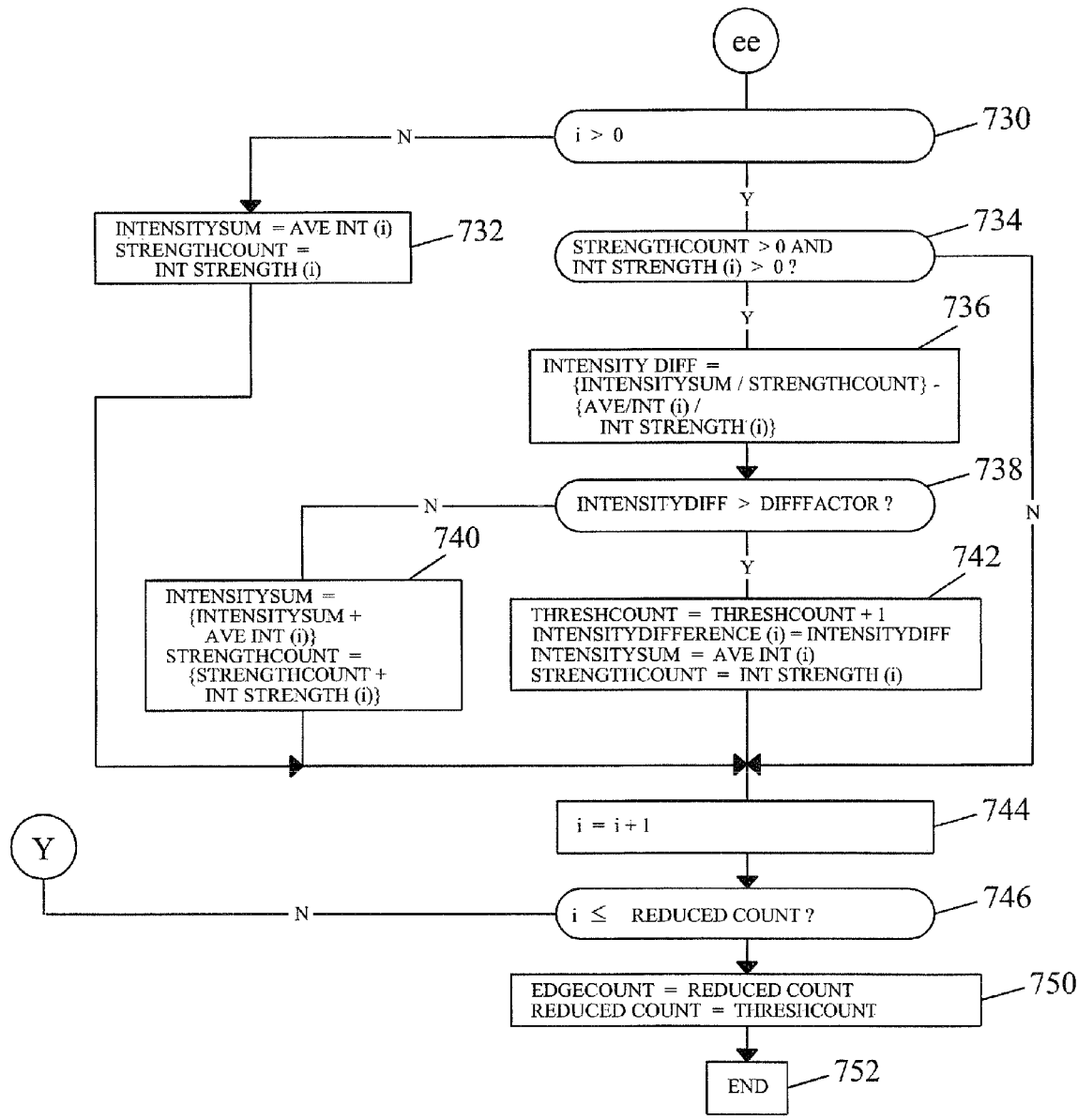
Figure 13-f

BLOOD PROCESSING APPARATUS WITH ROBUST AUTOMATED PROCESS CONTROL

CROSS REFERENCE TO RELATED APPLICATIONS

This application claims the benefit of U.S. Provisional Application No. 60/822,672 filed Aug. 17, 2006.

FIELD OF THE INVENTION

The present invention relates to an apparatus and method for separating particles or components of a fluid. The invention has particular advantages in connection with separating blood components, such as white blood cells and platelets.

This application is related to U.S. Pat. No. 5,722,926, issued Mar. 3, 1998; U.S. Pat. No. 5,951,877, issued Sep. 14, 1999; U.S. Pat. No. 6,053,856, issued Apr. 25, 2000; U.S. Pat. No. 6,334,842, issued Jan. 1, 2002; U.S. patent application Ser. No. 10/884,877 filed Jul. 1, 2004; U.S. patent application Ser. No. 10/905,353, filed Dec. 29, 2004; and U.S. patent application Ser. No. 11/163,969, filed Nov. 4, 2005.

DESCRIPTION OF THE RELATED ART

In the medical field, it is often necessary to separate blood into components. Whole blood consists of various liquid components and particle components. The liquid portion of blood is largely made up of plasma, and the particle components include red blood cells (erythrocytes), white blood cells (leukocytes), and platelets (thrombocytes). While these constituents have similar densities, their average density relationship, in order of decreasing density, is as follows: red blood cells, white blood cells, platelets, and plasma. In addition, the particle components are related according to size, in order of decreasing size, as follows: white blood cells, red blood cells, and platelets.

Typically, donated platelets are separated or harvested from other blood components using a centrifuge. White cells or other selected components may also be harvested. The centrifuge rotates a blood separation vessel to separate components within the vessel or reservoir using centrifugal force. In use, blood enters the separation vessel while it is rotating rapidly and centrifugal force stratifies the blood components, so that particular components may be separately removed. Components are removed through ports arranged within stratified layers of blood components.

White blood cells and platelets in plasma form a medium density stratified layer or "buffy coat". Because typical centrifuge collection processes are unable to consistently and satisfactorily separate white blood cells from platelets in the buffy coat, other processes have been added to improve results. One separation process is one known as centrifugal elutriation. In one common form of elutriation, a cell batch is introduced into a flow of liquid elutriation buffer, which carries the cell batch in suspension into a funnel-shaped chamber located on a spinning centrifuge. As additional liquid buffer solution flows through the chamber, the liquid sweeps smaller sized, slower-sedimenting cells toward an elutriation boundary within the chamber, while larger, faster-sedimenting cells migrate to an area of the chamber having the greatest centrifugal force.

When the centrifugal force and force generated by the fluid flow are balanced, the fluid flow is increased to force slower-sedimenting cells from an exit port in the chamber, while faster-sedimenting cells are retained in the chamber. If fluid flow through the chamber is increased, progressively larger, faster-sedimenting cells may be removed from the chamber.

The apparatus has a fluid separation chamber having a first frustro-conical segment adjacent a fluid inlet and radially inward therefrom, a second frustro-conical segment immediately adjacent the first frustro-conical segment and radially inward therefrom, the second frustro conical segment having a taper such that particles within the second frustro-conical segment are subjected to substantially equal and opposite centripetal and fluid flow forces. The taper of the second frustro-conical segment is selected based on the expected size of particles, such that at least particles of the average size of expected particles will be subjected to substantially equal and opposite centripetal and fluid forces. The apparatus has at least one pump controlling a rate of fluid flow through the fluid separation chamber, a camera configured to observe fluid flow with respect to the fluid separation chamber, and a controller receiving signals from the camera and controlling the motor and the pump.

For these and other reasons, there is a need to improve control of particle separation and/or separation of components of a fluid.

SUMMARY OF THE INVENTION

The present invention comprises a blood component separation apparatus having a rotor for centrifugally separating blood into phases such as red blood cells, white blood cells or buffy coat, or plasma. A camera monitors a separation chamber and image processing determines the location of boundaries. The apparatus controls the position of the boundaries by adjusting the speed of pumps or the rotor or both.

In a high-speed centrifuge for separating blood components, control of the interface between blood components presents significant control problems. The present apparatus controls the interface location by measuring light intensity in at least a first flux monitoring region in the collect port whereby the general level of the interface is set by, for example, detecting the presence or absence of RBC's in the collect port, and then by monitoring the interface in the phase boundary or interface monitoring region. The location of the interface is reliably detected by a series of image processing steps, which allow the apparatus to recognize a boundary or interface despite the high speed of the centrifuge rotor, the stroboscopic light used for observation, and the limitations of data processing time caused by the need for real-time response to changes in the interface location. Monitoring the interface in the interface monitoring region allows the apparatus to control the location of the interface with stability. The image processing steps for controlling the interface may comprise the steps of "spoiling" the image, "diffusing" the image, "edge detection", "edge linking", "region-based confirmation", and "interface calculation". These image processing steps will be described herein in connection with general flow chart representations for clarity. It will be understood that one skilled in the art would implement the programs in a selected programming language, such as C++ for example, but the programs could also be implemented in machine language, in firmware, or in dedicated circuitry without departing from the teachings set forth herein. "Spoiling" the image reduces the number of pixels to be examined preferentially on orthogonal axes oriented with respect to the expected location of the interface or phase boundary. For example, if the pixels of the image are oriented in rows parallel to the interface and in columns perpendicular to the interface or interfaces, the software might sample every third pixel along rows and every tenth pixel along columns or, more preferably, every pixel along rows and every tenth pixel along columns. This reduces the number of pixels to be processed, while retaining sufficient detail in a preferred direction to detect changes in the interface location. "Diffusing" the image smoothes out small oscillations in the interface boundary, making the location of the interface more distinct. "Edge detection" computes the rate of change in pixel intensity (that is, the derivative of the pixel intensity) as a function of distance in x (parallel to rotation) and y (perpendicular to rotation or radially with respect to the centrifuge) directions. Locations where the derivatives reach maxima indicate sharp intensity changes between pixels, which may represent an interface. "Edge linking" connects adjacent maxima. A chain of such connected maxima is identified as an edge of an interface if the chain is sufficiently long. The length may be predetermined empirically. Short chains are ignored as waves or other flow phenomenon. To confirm that the boundaries have actually been detected, the software uses the potential boundaries to form regions on either sides of the boundary and determines the average intensity of pixels in each region. "Region-based confirmation" creates a pseudo image of the regions that qualify as distinct, that is, having at least a predetermined difference in average intensity, and shades each region differently. "Final edge calculation" uses the points where the shade changes in the pseudo image, averages the y (radial) displacement of these points and recognizes this average radial location as the true interface position.

This image processing is fast enough to respond to the high speed of the centrifuge in real time, yet sufficiently robust to detect subtle changes in the location of the interface or interfaces such that rotor speed or pump speed can be changed to correct and control the interface location. Responding to changes in intensity in the flux monitoring region would not be rapid enough to maintain the quality of blood product being collected.

Collect port measuring of intensity in the flux monitoring region allows measurement of cellular material leaving through the collect port in real time. Statistical measures may be used for such parameters as the hematocrit of collected blood product, allowing for more accurate collection of a desired type of product.

It is an object of the present invention to provide a monitoring system for a density centrifuge blood processing system for separating fluid components and having a separation chamber rotating about a central rotation axis, comprising a light source in optical communication with said density centrifuge blood processing system for providing an incident light beam for illuminating an observation region on said density centrifuge blood processing system, thereby generating light transmitted, scattered or both from said observation region; a light collection element in optical communication with said density centrifuge blood processing system for collecting at least a portion of said light transmitted, scattered, or both from said observation region and for directing at least a portion of said light transmitted, scattered or both from said observation region onto a two-dimensional detector; and the two-dimensional detector positioned to receive and detect said light transmitted, scattered or both from said observation region provided by said light collection element, said two-dimensional detector having a reduced sensitivity in a direction parallel to an expected phase boundary between said fluid components as compared to a sensitivity perpendicular to said expected phase boundary.

It is also an object of the invention to provide a monitoring system for a density centrifuge blood processing system for separating fluid components having computational apparatus receiving intensities for selected pixels and determining a diffusion function to reduce detection of false phase boundaries between blood components. Another object is having a diffusion function comprising second partial derivatives of the intensity in at least two directions and a partial derivative of intensity with respect to time. Also, the diffusion function may compute the intensity of a pixel by computing $$I_{t+1} = I_t + \alpha^*(I_{ij-1} + I_{i-1j} + I_{i+1j} + I_{ij+1} - 4^*I_{ij})$$

Where $\alpha$ is an empirical constant;
i and j are special directions;
$I_{i,j}$ is an intensity of a pixel at a location;
$I_{ij-1}$; $I_{i-1j}$; $I_{i+1j}$; and $I_{ij+1}$ are intensities of pixels adjacent said pixel at said location;
$I_t$ is an intensity of a pixel at a selected time; and
$I_{t+1}$ is a diffused pixel at a next time.

Yet another object of the invention is a monitoring system for a density centrifuge blood processing system for separating fluid components having computational apparatus scanning a field of pixel values to detect phase boundaries between blood components and wherein the computational apparatus may determine a set of gradients of the pixel values. It may also be an object of the monitoring system that gradients that exceed adjacent gradients in a selected direction are assigned a value representing a phase boundary and pixel locations for the gradients that do not exceed adjacent gradients in the selected direction are assigned a value representing a phase.

Another aspect of the monitoring system may be a computational apparatus scanning a field of pixel values to detect a plurality of edges on phase boundaries between blood components; and linking adjacent edges that are sufficiently close. An additional feature is a monitoring system for a density centrifuge blood processing system for separating fluid having computational apparatus that scans a field of pixel values to detect a phase boundaries between blood components; and assign pixels to regions with respect to the detected boundaries.

Also, a monitoring system for a density centrifuge blood processing system for separating fluid components may have computational apparatus receiving intensities for selected pixels and determining a diffusion function to accentuate detection of phase boundaries between blood components; scanning a field of pixel values to detect phase boundaries between blood components by determining a set of gradients of said pixel values; linking adjacent edges that are recognized as a phase boundary if the length of said linked adjacent edges is greater than a predetermined minimum length; assigning pixels to regions with respect to said detected boundaries; determining an average intensity for pixels in each of said regions; comparing the average intensity of pixels in adjacent regions; combining said adjacent regions into a common region if a difference of said average intensities does not exceed a predetermined limit; and re-determining said phase boundaries based on said combined regions.

Furthermore, it may also be an object of the invention to provide a monitoring system for a density centrifuge blood processing system for separating fluid components a light source illuminating an observation region wherein phase boundaries between separated blood components may be observed and a collect port measuring area wherein blood components flowing through said collect port may be observed wherein control means responds to changes in detected blood component flow to establish a correct phase boundary level and further responds to changes in observed phase boundaries to maintain a consistent phase boundary level.

It is to be understood that both the foregoing general description and the following detailed description are exemplary, and are intended to provide further explanation of the invention as claimed.

BRIEF DESCRIPTION OF THE DRAWINGS

FIG. 7 shows the relationship of FIG. 7-a through FIG. 7-d, which illustrate a general program for controlling a blood processing centrifuge apparatus.

FIG. 9 shows the relationship of FIG. 9-a through FIG. 9-d, which illustrate a subroutine of the program of FIG. 7, showing "diffuse" image processing.

FIG. 11 shows the relationship of FIG. 11-a through FIG. 11-d, which illustrate a subroutine of the program of FIG. 7, showing "edge linker" image processing.

FIG. 12 shows the relationship of FIG. 12-a through FIG. 12-b, which illustrate a sub-subroutine of the subroutine of FIG. 11, showing "local check" data processing.

FIG. 13 shows the relationship of FIG. 13-a through FIG. 13-f, which illustrate a subroutine of the program of FIG. 7, showing "region" image processing.

DETAILED DESCRIPTION

The present invention preferably comprises a blood processing apparatus having a camera control system, as disclosed in U.S. patent application Ser. Nos. 10/884,877 and 10/905,353. It may also be practiced with a TRIMA® blood component centrifuge manufactured by Gambro BCT, Inc. of Colorado or, alternatively, with a COBE® SPECTRA™ single-stage blood component centrifuge also manufactured by Gambro BCT, Inc. Both the TRIMA® and the SPECTRA™ centrifuges incorporate a one-omega/two-omega sealless tubing connection as disclosed in U.S. Pat. No. 4,425,112 to Ito. The SPECTRA™ centrifuge also uses a single-stage blood component separation channel substantially as disclosed in U.S. Pat. No. 4,094,461 to Kellogg et al. and U.S. Pat. No. 4,647,279 to Mulzet et al. The invention could also be practiced with a TRIMA® or TRIMA ACCEL® centrifugal separation system or other types of centrifugal separator. The method of the invention is described in connection with the aforementioned blood processing apparatus and camera control system for purposes of discussion only, and this is not intended to limit the invention in any sense.

Figure 1:
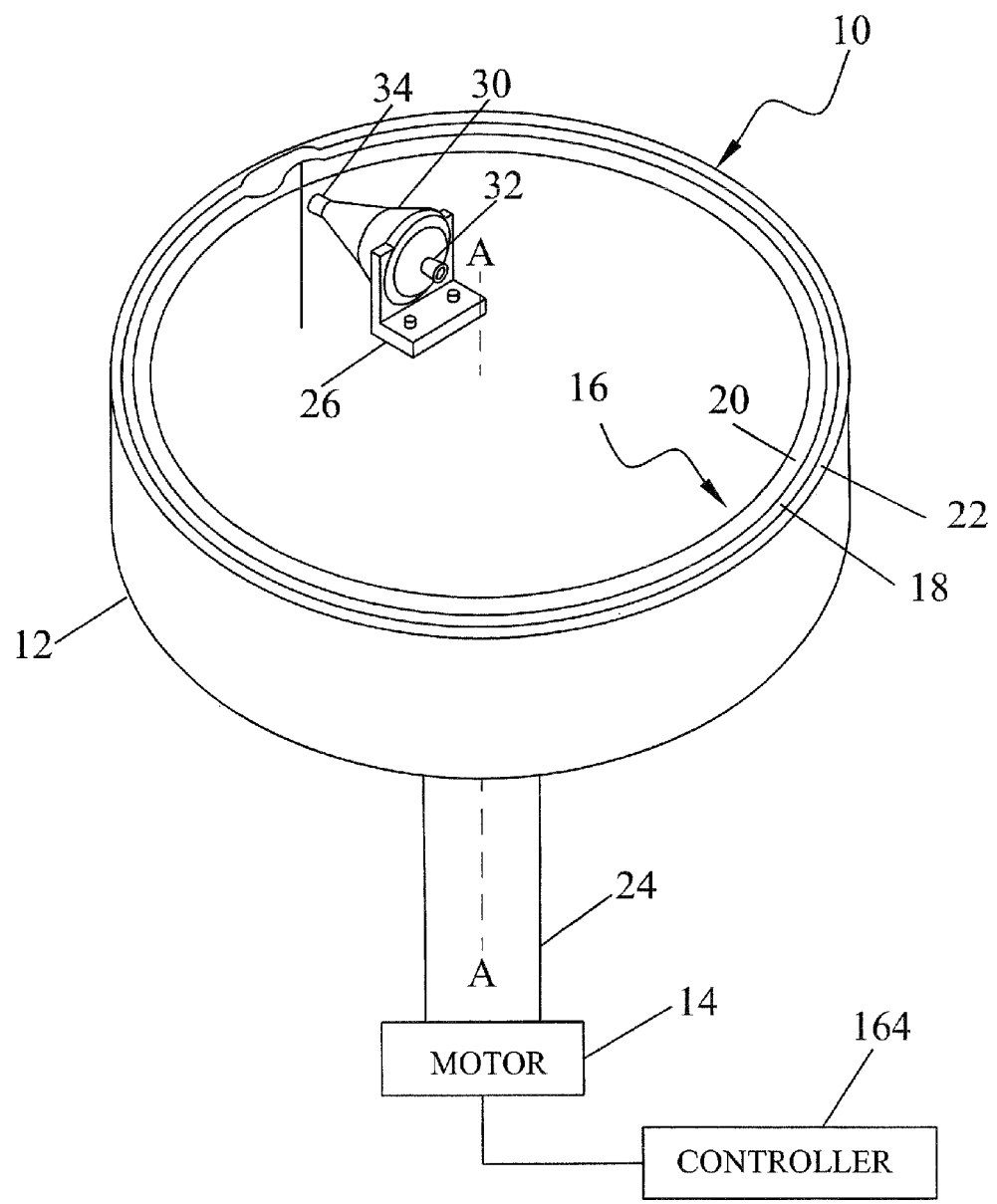
FIG. 1 is a partial perspective, schematic view of a blood processing centrifuge apparatus including a fluid chamber.

As embodied herein and illustrated in FIG. 1, a centrifuge apparatus 10 has a centrifuge rotor 12 coupled to a motor 14 so that the centrifuge rotor 12 rotates about its axis of rotation A-A. The motor 14 is coupled to the rotor 12 directly or indirectly through a shaft 24 connected to the rotor 12. Alternately, the shaft 24 may be coupled to the motor 14 through a gearing transmission (not shown).

Figure 4:
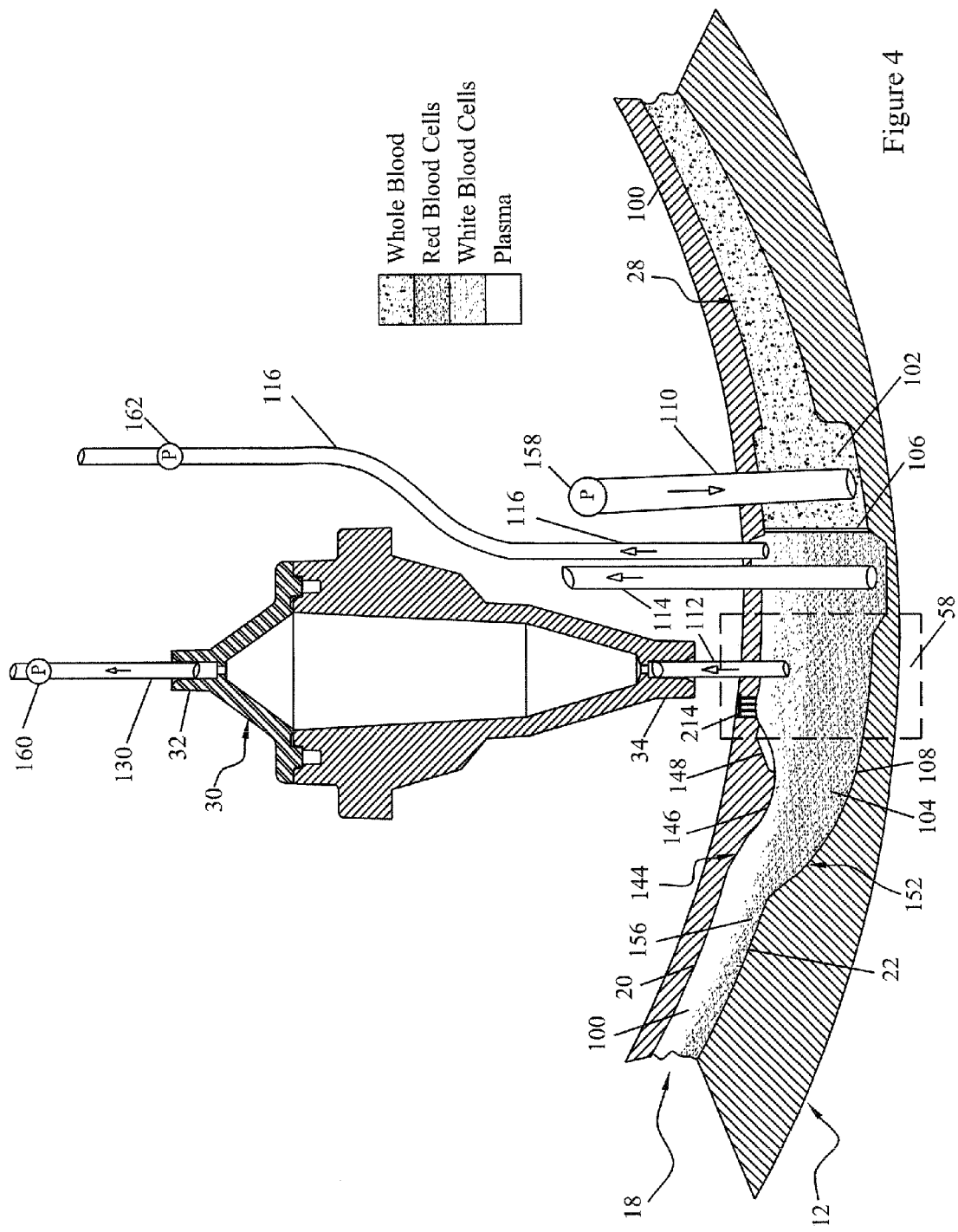
FIG. 4 is a partial cross-sectional, schematic view of a portion of a separation vessel and the fluid chamber mounted on a centrifuge rotor of FIG. 1.

The rotor 12 has a retainer 16 including a passageway or annular groove 18 having an open upper surface adapted to receive a separation vessel 28, shown in pertinent part in FIG. 4. The groove 18 completely surrounds the rotor's axis of rotation A-A and is bounded by an inner wall 20 and an outer wall 22 spaced apart from one another to define the groove 18 therebetween. Although the groove 18 shown in FIG. 1 completely surrounds the axis of rotation A-A, the groove could partially surround the axis A-A if the separation vessel is not annular. Preferably, a substantial portion of the groove 18 has a constant radius of curvature about the axis of rotation A-A and is positioned at a maximum possible radial distance on the rotor 12. This shape ensures that substances separated in the separation vessel 28 undergo relatively constant centrifugal forces as they pass from an inlet portion to an outlet portion of the separation vessel 28.

As shown in FIG. 1, a bracket 26 is provided on a top surface of the rotor 12. The bracket 26 releasably holds a fluid chamber 30 on the rotor 12 so that an outlet 32 of the fluid chamber 30 is positioned closer to the axis of rotation A-A than an inlet 34 of the fluid chamber 30. The bracket 26 preferably orients the fluid chamber 30 on the rotor 12 with a longitudinal axis of the fluid chamber 30 in a plane transverse to the rotor's axis of rotation A-A. In addition, the bracket 26 is preferably arranged to hold the fluid chamber 30 on the rotor 12 with the fluid chamber outlet 32 facing the axis of rotation A-A. Although the fluid chamber 30 is shown on a top surface of the rotor 12, the fluid chamber 30 could also be secured to the rotor 12 at alternate locations, such as beneath the top surface of the rotor 12.

Figure 2:
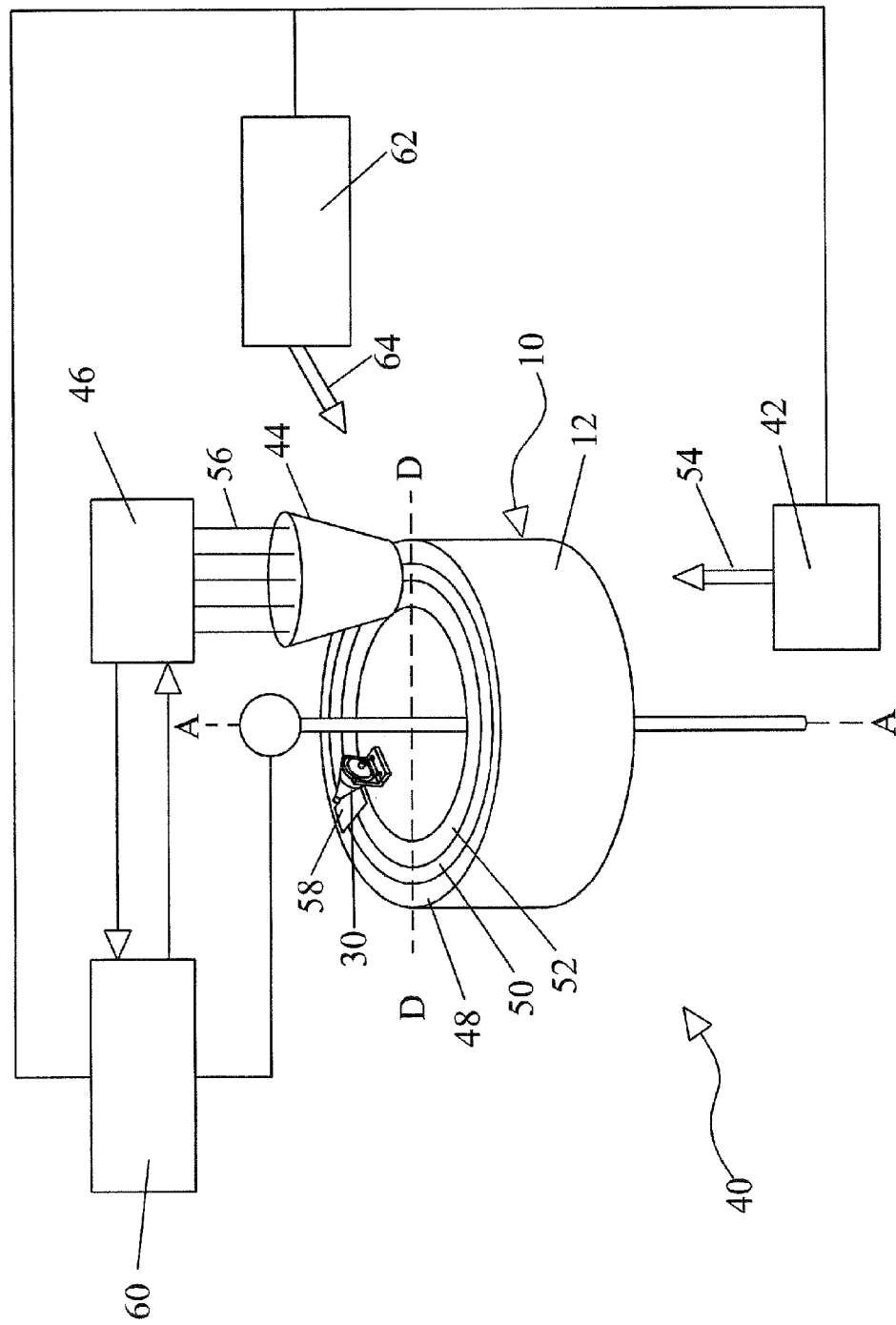
FIG. 2 is a partial perspective, schematic view of the centrifuge apparatus and a control camera.

FIG. 2 schematically illustrates an exemplary embodiment of an optical monitoring system 40 capable of measuring a distribution of scattered and/or transmitted light intensities corresponding to patterns of light originating from an observation region on the separation vessel 28. The monitoring system 40 comprises light source 42, light collection element 44, and detector 46. Light source 42 is in optical communication with the centrifuge apparatus 10 comprising rotor 12, which rotates about central rotation axis A-A. Rotation about central rotation axis A-A results in separation of a blood sample in the separation vessel 28 into discrete blood components along a plurality of rotating separation axes oriented orthogonal to the central rotation axis A-A.

Light source 42 provides incident light beam 54, which stroboscopically illuminates an observation region 58 when the observation region 58 passes under the light collection element 44. Light source 42 is capable of generating an incident light beam, a portion of which is transmitted through at least one blood component undergoing separation in separation vessel 28. At least a portion of scattered and/or transmitted light 56 from the observation region 58 is collected by light collection element 44. Light collection element 44 is capable of directing at least a portion of the collected light 56 onto detector 46. The detector 46 detects patterns of scattered and/or transmitted light 56 from the observation region. Optionally, the observation region 58 may also be illuminated by an upper light source 62, which is positioned on the same side of the separation chamber as the light collection element 44 and detector 46. Upper light source 62 is positioned such that it generates an incident beam 64, which is scattered by the blood sample and/or centrifuge. A portion of the light from upper light source 62 is collected by light collection element 44 and detected by detector 46, thereby measuring a distribution of scattered and/or transmitted light intensities.

Distributions of scattered and/or transmitted light intensities comprise images corresponding to patterns of light originating from the observation region 58. The images may be monochrome images, which provide a measurement of the brightness of separated blood components along the separation axis. Alternatively, the images may be color images, which provide a measurement of the colors of separated blood components along the separation axis. Observation region 58 is positioned on a portion of the density centrifuge 10, preferably on the separation vessel 28. The fluid chamber 30 may also be an observation region, as explained below. In the exemplary embodiment illustrated in FIG. 6, separated blood components and phase boundaries between optically differentiable blood components are viewable in observation region 58.

Detector 46 is also capable of generating output signals corresponding to the measured distributions of scattered and/or transmitted light intensities and/or images. The detector 46 is operationally connected to a device controller 60 capable of receiving the output signals. Device controller 60 displays the measured intensity distributions, stores the measured intensity distributions, processes measured intensity distributions in real time, transmits control signals to various optical and mechanical components of the monitoring system and centrifuge or any combination of these. Device controller 60 is operationally connected to centrifuge apparatus 10 and is capable of adjusting selected operating conditions of the centrifuge apparatus, such as the flow rates of cellular and non-cellular components out of the separation vessel 28 or fluid chamber 30, the position of one or more phase boundaries, rotational velocity of the rotor about central rotation axis A-A, the infusion of anticoagulation agents or other blood processing agents to the blood sample, or any combination of these.

Device controller 60 can also be operationally connected to light source 42 and/or upper light source 62. Device controller 60 and/or detector 46 are capable of generating output signals for controlling illumination conditions. For example, output signals from the detector 46 can be used to control the timing of illumination pulses, illumination intensities, the distribution of illumination wavelengths and/or position of light source 42 and/or upper light source 62. Device controller 60 and detector 46 are in two-way communication, and the device controller sends control signals to detector 46 to selectively adjust detector exposure time, detector gain and to switch between monochrome and color imaging.

Light sources comprise light emitting diode sources capable of generating one or more incident beams for illuminating an observation region on the centrifuge. A plurality of lamps may be positioned to illuminate a single side or multiple sides of the centrifuge apparatus 10. Light emitting diodes and arrays of light emitting diode light sources are preferred for some applications because they are capable of generating precisely timed illumination pulses. Preferred light sources generate an incident light beam having a substantially uniform intensity, and a selected wavelength range.

The optical monitoring system comprises a plurality of light sources, each capable of generating an incident light beam having a different wavelength range, for example, a combination of any of the following: white light source, red light source, green light source, blue light source and infra red light source. Use of a combination of light sources having different wavelength ranges is beneficial for discriminating and characterizing separated blood fractions because absorption constants and scattering coefficients of cellular and non-cellular components of blood vary with wavelength. For example, a component containing red blood cells is easily distinguished from platelet-enriched plasma by illumination with light having wavelengths selected over the range of about 500 nm to about 600 nm, because the red blood cell component absorbs light over this wavelength significantly more strongly that the platelet-enriched plasma component. In addition, use of multiple colored light sources provides a means of characterizing the white blood cell type in an extracted blood component. As different white blood cell types have different absorption and scattering cross sections at different wavelengths, monitoring transmitted and/or scattered light from a white cell-containing blood component provides a means of distinguishing the various white blood cell types in a blood component and quantifying the abundance of each cell-type.

The light sources provide a continuous incident light beam or a pulsed incident light beam. Pulsed light sources are switched on and off synchronously with the rotation of the rotor to illuminate an observation region having a substantially fixed position on the rotor. Alternatively, pulsed light sources of the present invention can be configured such that they can be switched on and off at different angular positions, synchronous with the rotation of the rotor, illuminating different observation regions for each full rotation. This alternative embodiment provides a method of selectively adjusting the location of the observation region and, thereby, probing different regions of the separation chamber or of the fluid chamber 30. Triggering of illumination pulses may be based on the rotational speed of the centrifuge or on the angular position of the separation chamber or the fluid chamber 30 as detected by optical or electronic methods well known in the art. Triggering may be provided by trigger pulses generated by the device controller 60 and/or detector 46.

Figure 3:
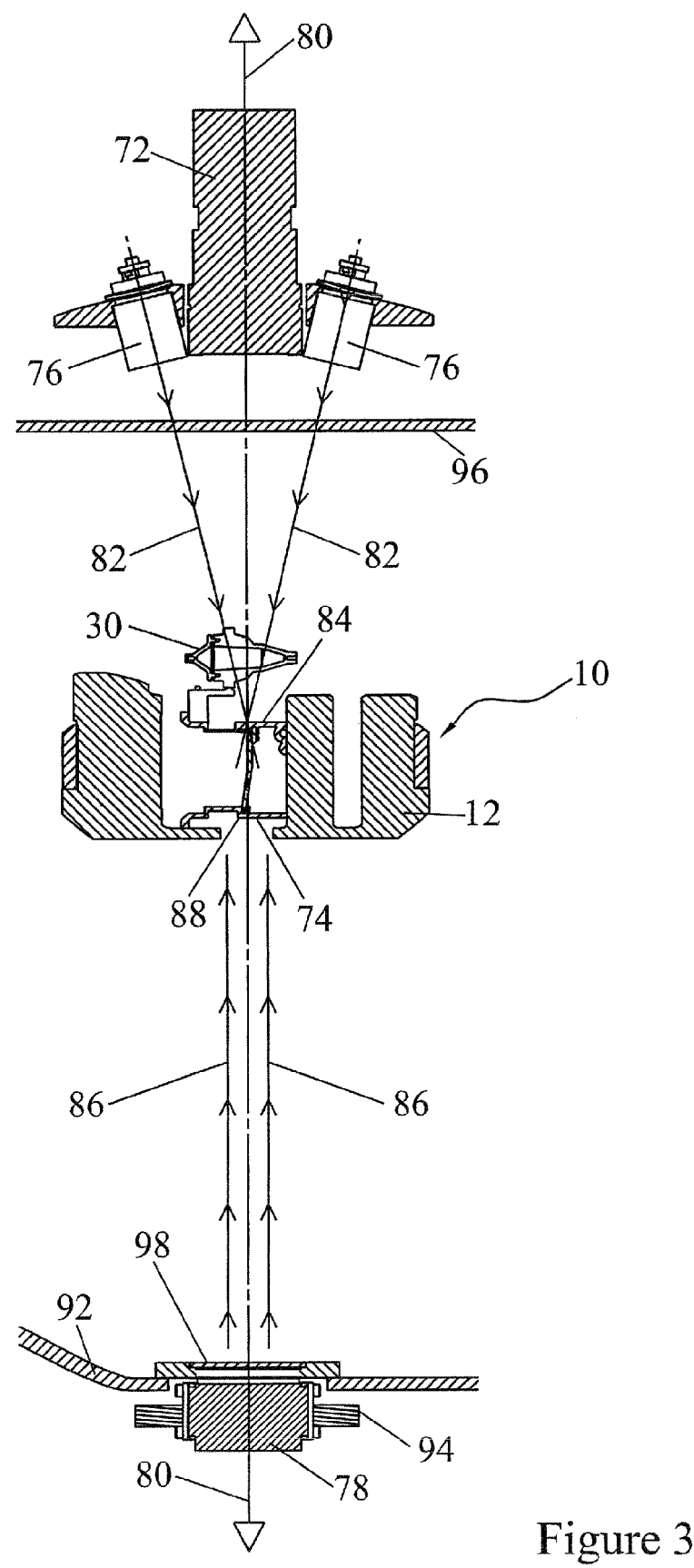
FIG. 3 is a partial cross-sectional view of blood processing apparatus of FIG. 2, including the fluid chamber of FIG. 1.

FIG. 3 is a cutaway view corresponding to cutaway of the optical monitoring system 40. The illustrated optical monitoring system 40 comprises CCD camera 72 (CMOS, APS or other cameras could also be used) equipped with a fixed focus lens system (corresponding to the light collection element 44 and detector 46), an optical cell 74 (corresponding to the observation region 58), an upper LED light source 76 (corresponding to the upper light source 62), and a bottom pulsed LED light source 78 (corresponding to the light source 42). As illustrated in FIG. 3, CCD camera 72 is in optical communication with optical cell 74 and positioned to intersect optical axis 80. Upper LED light source 76 is in optical communication with optical cell 74 and is positioned such that it is capable of directing a plurality of collimated upper light beams 82, propagating along propagation axes that intersect optical axis 80, onto the top side 84 of optical cell 74. Bottom pulsed LED light source 78 is also in optical communication with optical cell 74 and is positioned such that it is capable of directing a plurality of collimated bottom light beams 86, propagating along optical axis 80, onto the bottom side 88 of optical cell 74.

CCD camera 72 may be positioned such that the focal plane of the fixed focus lens system is substantially co-planar with selected optical surfaces of optical cell 74, such as optical surfaces corresponding to an interface monitoring region, calibration markers, one or more extraction ports and one or more inlets. The CCD camera 72 is separated from the center of the fixed focus lens system by a distance along optical axis 80 such that an image corresponding to selected optical surfaces of optical cell 74 is provided on the sensing surface of the CCD camera. This optical configuration allows distributions of light intensities comprising images of rotating optical cell 74 or of fluid chamber 30 to be measured and analyzed in real time.

Referring to FIG. 3, first transparent plate 96 is provided between CCD camera 72 and optical cell 74, and second transparent plate 98 is provided between bottom LED light source 78 and optical cell 74. First and second transparent plates 96 and 98 physically isolate CCD camera 72, upper LED light source 76 and bottom LED light source 78 from optical cell 74 so that these components will not contact a sample undergoing processing in the event of sample leakage from the separation chamber. In addition, first and second transparent plates 96 and 98 minimize degradation of CCD camera 72, upper LED light source 76 and bottom LED light source 78 due to unwanted deposition of dust and other contaminants that can be introduced to the system upon rotation of the separation chamber and filler. Further, first and second transparent plates 96 and 98 also allow a user to optimize the alignment of the camera, upper LED light source and bottom LED light source without exposure to a blood sample in the separation chamber. First and second transparent plates 96 and 98 can comprise any material capable of transmitting at least a portion of upper and bottom illumination light beams 82 and 86. Exemplary materials for first and second transparent plates 96 and 98 include, but are not limited to, glasses such as optical quality scratch resistant glass, transparent polymeric materials such as transparent plastics, quartz and inorganic salts.

FIG. 4 schematically illustrates a portion of the separation vessel 28 and fluid chamber 30 mounted on the rotor 12. The separation vessel 28 has a generally annular flow path 100 and includes an inlet portion 102 and outlet portion 104. A wall 106 prevents substances from passing directly between the inlet and outlet portions 102 and 104 without first flowing around the generally annular flow path 100 (e.g., counter-clockwise in FIG. 4).

A radial outer wall 108 of the separation vessel 28 is positioned closer to the axis of rotation A-A in the inlet portion 102 than in the outlet portion 104. During separation of blood components, this arrangement causes formation of a very thin and rapidly advancing red blood cell bed in the separation vessel 28 between the inlet portion 102 and outlet portion 104. The red blood cell bed reduces the amount of blood components required to initiate a separation procedure, and also decreases the number of unnecessary red blood cells in the separation vessel 28. The red blood cell bed substantially limits or prevents platelets from contacting the radial outer wall 108 of the separation vessel 28. This is believed to reduce clumping of platelets caused when platelets contact structural components of centrifugal separation devices.

The inlet portion 102 includes an inflow tube 110 for conveying a fluid to be separated, such as whole blood, into the separation vessel 28. During a separation procedure, substances entering the inlet portion 102 follow the flow path 100 and stratify according to differences in density in response to rotation of the rotor 12. The outlet portion 104 includes first, second, and third outlet lines 112, 114, 116 for removing separated substances from the separation vessel 28. Preferably, each of the components separated in the vessel 28 is collected and removed in only one area of the vessel 28, namely the outlet portion 104. In addition, the separation vessel 28 preferably includes a substantially constant radius except in the region of the outlet portion 104 where the outer wall of the outlet portion 104 is preferably positioned farther away from the axis of rotation A-A to allow for outlet ports of the lines 112, 114, and 116 to be positioned at different radial distances and to create a collection pool with greater depth for the high density red blood cells. The outlet port of line 114 is farther from the axis of rotation A-A than the other ports to remove higher density components, such as red blood cells. The port of line 116 is located closer to the axis of rotation A-A than the other ports to remove the least dense components separated in the separation vessel 28, such as plasma. The first line 112 collects intermediate density components and, optionally, some of the lower density components. The second and third lines 114 and 116 are positioned downstream from first line 112 to collect the high and low density components.

The positions of the interfaces are controlled by the CCD camera 72 monitoring the position of the interface and controlling flow of liquid and/or particles in response to the monitored position. Further details concerning the structure and operation of the separation vessel 28 are described in U.S. patent application Ser. No. 10/884,877 and also in U.S. Pat. No. 4,094,461 to Kellogg et al. and U.S. Pat. No. 4,647,279 to Mulzet et al.

A ridge 144 extends from the inner wall 20 of the groove 18 toward the outer wall 22 of the groove 18. When the separation vessel 28 is loaded in the groove 18, the ridge 144 deforms semi-rigid or flexible material in the outlet portion 104 of the separation vessel 28 to form a trap dam 146 in the separation vessel 28, upstream from the first line 112. The trap dam 146 extends away from the axis of rotation A-A to trap a portion of lower density substances, such as priming fluid and/or plasma, along an inner portion of the separation vessel 28 located upstream the trap dam 146. These trapped substances help convey platelets to the outlet portion 104 and first line 112 by increasing plasma flow velocities next to the layer of red blood cells in the separation vessel 28 to scrub platelets toward the outlet portion 104. A downstream portion 148 of the trap dam 146 has a relatively gradual slope extending in the downstream direction toward the axis of rotation A-A, which limits the number of platelets (intermediate density components) that become re-entrained (mixed) with plasma (lower density components) as plasma flows along the trap dam 146. In addition, the gradual slope of the downstream portion 148 reduces the number of platelets that accumulate in the separation vessel 28 before reaching the first collection port 120.

Figure 5:
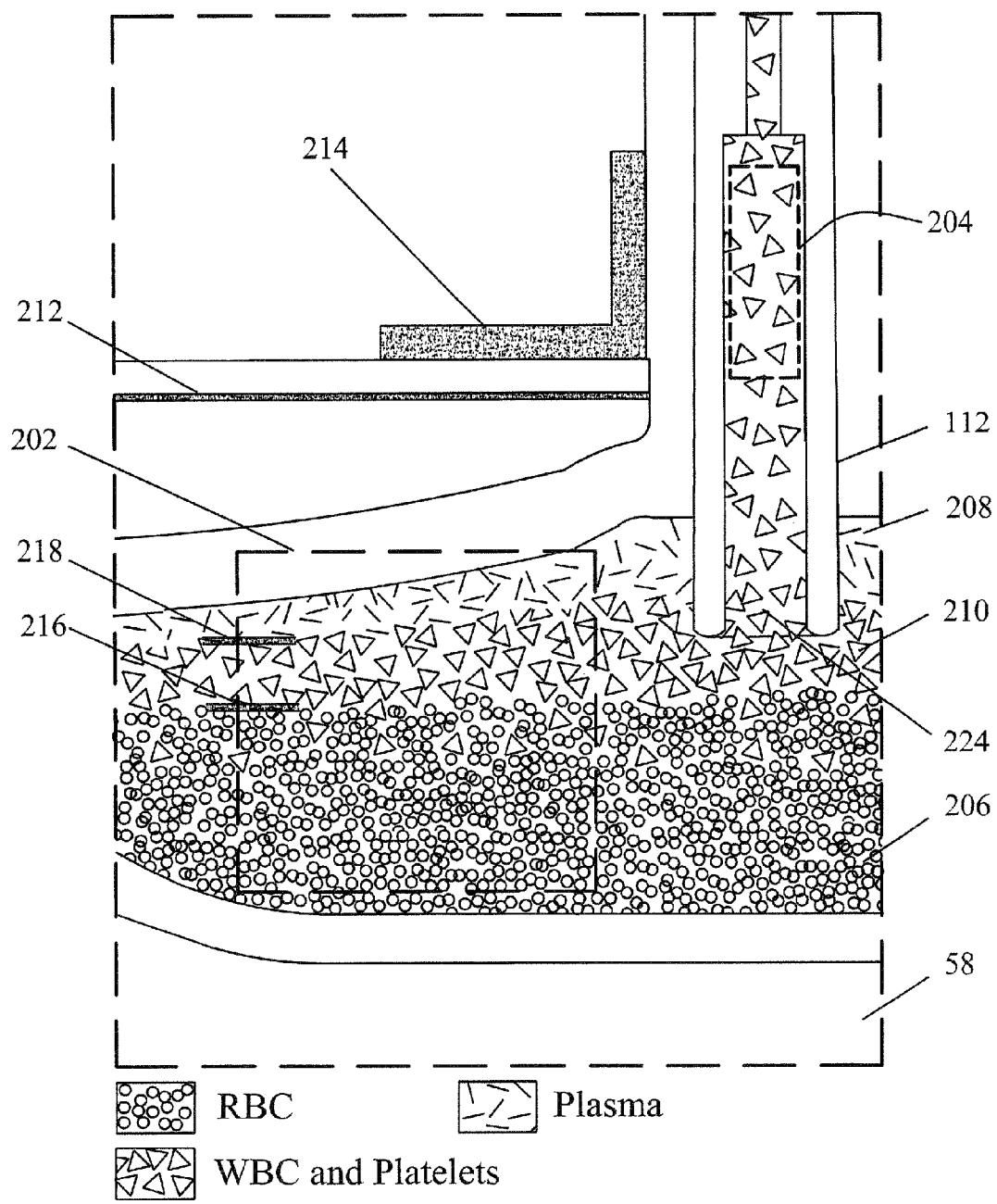
FIG. 5 is a plan view of a separation chamber of the separation vessel of FIG. 4.

The camera 44 is generally focused on the separation vessel and stroboscopic illumination allows an observation region 58 around the first, second, and third lines 112, 114, and 116 to be observed. Using information gathered through the camera, the controller 60 regulates the position of interfaces between various blood components, such as plasma, buffy coat (containing monocytes and/or white blood cells and platelets) and red blood cells by controlling the pumps 158, 168, and 162. FIG. 5 shows an image of the observation region 58 generated by the methods of US patent application Ser. No. 10/884,877 corresponding to the separation of a human blood sample and extraction of a separated white blood cell-containing blood component. The observation region 58 shown in FIG. 5 includes a phase boundary monitoring region 202 and an extraction or collect port monitoring region 204. Visible in phase boundary monitoring region 202 are a red blood cell component 206, a plasma component 208 and a mixed-phase buffy coat layer 210, which has both white blood cells and platelets. Several calibration markers are also apparent in the image in FIG. 5. The edge 212 of the optical cell comprises a first calibration marker for determining the absolute position of phase boundaries between optically differentiable blood components. A series of bars 214 having a thickness of 1 mm and known scattering and absorption characteristics comprises a second calibration marker useful for optimizing the focusing of the light collection element and indicating the positions and physical dimensions of the phase boundary monitoring region 202 and the white blood cell collect port monitoring region 204. Light intensities transmitted through the phase boundary monitoring region 202 are acquired as a function of time and analyzed in real time to provide measurements of the position of the phase boundary 216 between red blood cell component 206 and buffy coat layer 210 and the phase boundary 218 between the buffy coat layer 210 and plasma component 208. All boundary layer positions are measured relative to the edge of the optical cell 212.

Collect port monitoring region 204 monitors flow in first line 112 of the optical cell for extracting a blood component, for example, white blood cells. The apparatus responds to changes in detected blood component flow to establish a correct phase boundary level and further responds to changes in observed phase boundaries to maintain a consistent phase boundary level. The system discriminates between a plasma flow condition, a white blood cell flow condition, and a red blood cell flow condition, and can detect pump-induced flow variation in the blood component flow in said collect port measuring area. A plasma signal limit and a red blood cell signal limit may be set and the flow of fluid adjusted based on said limits. The system derives a statistical measure of fluid flow in the collect port measuring area, which may be a moving median of the average value of intensity of pixels in the collect port measuring area.

In this example, first line 112 having orifice 224 is configured to collect white blood cells in the human blood sample and extends a distance along the separation axis such that it terminates proximate to the buffy coat layer in the rotating separation chamber. The two-dimensional distribution of light intensities of light transmitted through the collect port in the collect port monitoring region 204 depends on the concentration, and spatial distribution and cell-type of cellular material exiting the separation chamber. Light intensities transmitted through the collect port monitoring region 204 are acquired as a function of time and analyzed to characterize the composition and flux of cellular material out of the separation chamber. As cellular materials, such as white blood cells and red blood cells, absorb and scatter light from the light sources, passage of cellular material through the extraction port decreases the observed light intensities.

Referring again to FIG. 4, the outer wall 22 of the groove 18 preferably includes a gradual sloped portion 152 facing the ridge 144 in the inner wall 20. When the separation vessel 28 is loaded in the groove 18, the gradual sloped portion 152 deforms semi-rigid or flexible material in the outlet portion 104 of the separation vessel 28 to form a relatively smooth and gradual sloped segment in a region of the vessel 28 across from the trap dam 146, which slopes gradually away from the axis of rotation A-A to increase the thickness of a layer of high-density fluid components, such as red blood cells, formed across from the trap dam 146.

The first collection line 112 is connected to the fluid chamber inlet 34 to pass the intermediate density components into the fluid chamber 30. Components initially separated in the separation vessel 28 are further separated in the fluid chamber 30. For example, white blood cells could be separated from plasma and platelets in the fluid chamber 30. This further separation preferably takes place by forming a saturated fluidized bed of particles, such as white blood cells, in the fluid chamber 30. The fluid chamber 30 may be formed of a transparent or translucent co-polyester plastic, such as PETG, to allow viewing of the contents within the chamber interior with the aid of the camera during a separation procedure.

As schematically shown in FIG. 4, a plurality of pumps 158, 160, and 162 are provided for adding and removing substances to and from the separation vessel 28 and fluid chamber 30. An inflow pump 158 is coupled to the inflow line 110 to supply the substance to be separated, such as whole blood, to the inlet portion 102. In addition, a first collection pump 160 is flow coupled to the outflow tubing 130 connected to the fluid chamber outlet 32, and a second collection pump 162 is flow coupled to the third collection line 116. The first collection pump 160 draws liquid and particles from the fluid chamber outlet 32 and causes liquid and particles to enter the fluid chamber 30 via the fluid chamber inlet 34. The second collection pump 162, on the other hand, removes primarily low-density substances from the separation vessel 28 via the third line 116.

The pumps 158, 160, and 162 are peristaltic pumps or impeller pumps configured to prevent significant damage to blood components. However, any fluid pumping or drawing device may be provided. In an alternative embodiment (not shown), the first collection pump 160 may be fluidly connected to the fluid chamber inlet 34 to directly move substances into and through the fluid chamber 30. In addition, the pumps 158, 160, and 162 may be mounted at any convenient location. The inflow pump 150 and the first collection pump 160 may be configured so that substances do not bypass these pumps when they are paused. For example, when the first collection pump 160 is temporarily paused, substances pumped by the second collection pump 162 flow into the fluid chamber outlet 32 rather than bypassing the pump 160 and flowing in the opposite direction.

The apparatus 10 further includes a controller 164 (FIG. 1) connected to the motor 14 to control rotational speed of the rotor 12. The controller 164 is connected to the pumps 158, 160, and 162 to control the flow rate of substances flowing to and from the separation vessel 28 and the fluid chamber 30. The controller 164 maintains a saturated fluidized bed of first particles within the fluid chamber 30 to cause second particles to be retained in the fluid chamber 30. The controller 164 also preferably controls the operation and flow rate of the pumps 158, 160, 162 to permit the temporary purging of the fluid chamber 30. The controller 164 may include a computer having programmed instructions provided by a ROM or RAM as is commonly known in the art. The controller 164 may vary the rotational speed of the centrifuge rotor 12 by regulating frequency, current, or voltage of the electricity applied to the motor 14. Alternatively, the rotational speed can be varied by shifting the arrangement of a transmission (not shown), such as by changing gearing to alter a rotational coupling between the motor 14 and rotor 12. The controller 164 may receive input from a rotational speed detector (not shown) to constantly monitor the rotation speed of the rotor.

After loading the separation vessel 28 and fluid chamber 30 on the rotor 12, the separation vessel 28 and chamber 30 are initially primed with a low density fluid medium, such as air, saline solution, plasma, or another fluid substance having a density less than or equal to the density of liquid plasma. Alternatively, the priming fluid is whole blood itself. This priming fluid allows for efficient establishment of a saturated fluidized bed of platelets within the fluid chamber 30. When saline solution is used, the pump 158 pumps this priming fluid through the inflow line 110 and into the separation vessel 28 via the inlet line 110. The saline solution flows from the inlet portion 102 to the outlet portion 104 (counterclockwise in FIG. 4) and through the fluid chamber 30 when the controller 164 activates the pump 160. Controller 164 also initiates operation of the motor 14 to rotate the centrifuge rotor 12, separation vessel 28, and fluid chamber 30 about the axis of rotation A-A. During rotation, twisting of lines 110, 112, 114, 116, and 130 is prevented by a sealless one-omega/two-omega tubing connection as is known in the art and described in above-mentioned U.S. Pat. No. 4,425,112.

As the separation vessel 28 rotates, a portion of the priming fluid (blood or saline solution) becomes trapped upstream from the trap dam 146 and forms a dome of priming fluid (plasma or saline solution) along an inner wall of the separation vessel 28 upstream from the trap dam 146. After the apparatus 10 is primed, and as the rotor 12 rotates, whole blood or blood components are introduced into the separation vessel 28. When whole blood is used, the whole blood can be added to the separation vessel 28 by transferring the blood directly from a donor or patient through inflow line 110. In the alternative, the blood may be transferred from a container, such as a blood bag, to inflow line 110.

The blood within the separation vessel 28 is subjected to centrifugal force causing components of the blood components to separate. The components of whole blood stratify in order of decreasing density as follows: (1) red blood cells, (2) white blood cells, (3) platelets, and (4) plasma. The controller 164 regulates the rotational speed of the centrifuge rotor 12 to ensure that this particle stratification takes place. A layer of red blood cells (high density component(s)) forms along the outer wall of the separation vessel 28 and a layer of plasma (lower density component(s)) forms along the inner wall of the separation vessel 28. Between these two layers, the intermediate density platelets and white blood cells (intermediate density components) form a buffy coat layer. This separation takes place while the components flow from the inlet portion 102 to the outlet portion 104. Preferably, the radius of the flow path 100 between the inlet and outlet portions 102 and 104 is substantially constant to maintain a steady red blood cell bed in the outlet portion 104 even if flow changes occur.

In the outlet portion 104, platelet poor plasma flows through the third line 116. These relatively low-density substances are pumped by the second collection pump 162 through the third collection line 116. Red blood cells are removed via the second line 114. The red blood cells flow through the second collection line 114 and can then be collected and optionally recombined with other blood components or further separated. Alternately, these removed blood components may be re-infused into a donor or patient.

Accumulated platelets are removed via the first collection line 112 along with some of the white blood cells and plasma. As the platelets, plasma, white blood cells, and possibly a small number or red blood cells pass through the first collection line 112, these components flow into the fluid chamber 30, filled with the priming fluid, so that a saturated fluidized particle bed may be formed. The portion or dome of priming fluid (i.e. saline) trapped along the inner wall of the separation vessel 28 upstream from the trap dam 146 guides platelets so that they flow toward the first collection line 112. The trapped fluid reduces the effective passageway volume and area in the separation vessel 28 and thereby decreases the amount of blood initially required to prime the system in a separation process. The reduced volume and area also induces higher plasma and platelet velocities next to the stratified layer of red blood cells, in particular, to "scrub" platelets toward the first collection line 112. The rapid conveyance of platelets increases the efficiency of collection.

The controller 164 maintains the rotation speed of the rotor 12 within a predetermined rotational speed range to facilitate formation of this saturated fluidized bed. In addition, the controller 164 regulates the pump 160 to convey at least the plasma, platelets, and white blood cells at a predetermined flow rate through the first collection line 112 and into the inlet 34 of the fluid chamber 30. These flowing blood components displace the priming fluid from the fluid chamber 30. When the platelet and white blood cell particles enter the fluid chamber 30, they are subjected to two opposing forces. Plasma flowing through the fluid chamber 30 with the aid of pump 160 establishes a first viscous drag force when plasma flowing through the fluid chamber 30 urges the particles toward the outlet 32. A second centrifugal force created by rotation of the rotor 12 and fluid chamber 30 acts to urge the particles toward the inlet 34.

The controller 164 regulates the rotational speed of the rotor 12 and the flow rate of the pump 160 to collect platelets and white blood cells in the fluid chamber 30. As plasma flows through the fluid chamber 30, the flow velocity of the plasma decreases and reaches a minimum as the plasma flow approaches the maximum cross-sectional area of the fluid chamber 30. Because the rotating centrifuge rotor 12 creates a sufficient gravitational field in the fluid chamber 30, the platelets accumulate near the maximum cross-sectional area of the chamber 30, rather than flowing from the chamber 30 with the plasma. The white blood cells accumulate somewhat radially outward from the maximum cross-sectional area of the chamber 30. However, density inversion tends to mix these particles slightly during this initial establishment of the saturated fluidized particle bed.

The fluid chamber 30 is configured to allow cyclic collection of selected particles, such as white blood cells, followed by efficient evacuation of the cells into a collection bag. In contrast to other chamber designs for forming saturated fluidized beds, the fluid chamber described herein has particular application for the automated collection of blood components in that a bolus of cells having selected characteristics can be collected in the fluid chamber 30 and then flushed with low density fluid into a collection bag and these steps can be repeated multiple times, allowing a larger quantity of the selected cells to be collected from the donor or patient while reducing the amount of time necessary for the donation process. Collection of cells in the fluid chamber can be monitored by the camera 72 and the device controller 60. When a selected quantity of cells have been collected in the fluid chamber 30, the flow of plasma through the chamber can be increased and the collected cells can be washed out of the chamber and directed into a collection bag.

Figure 6:
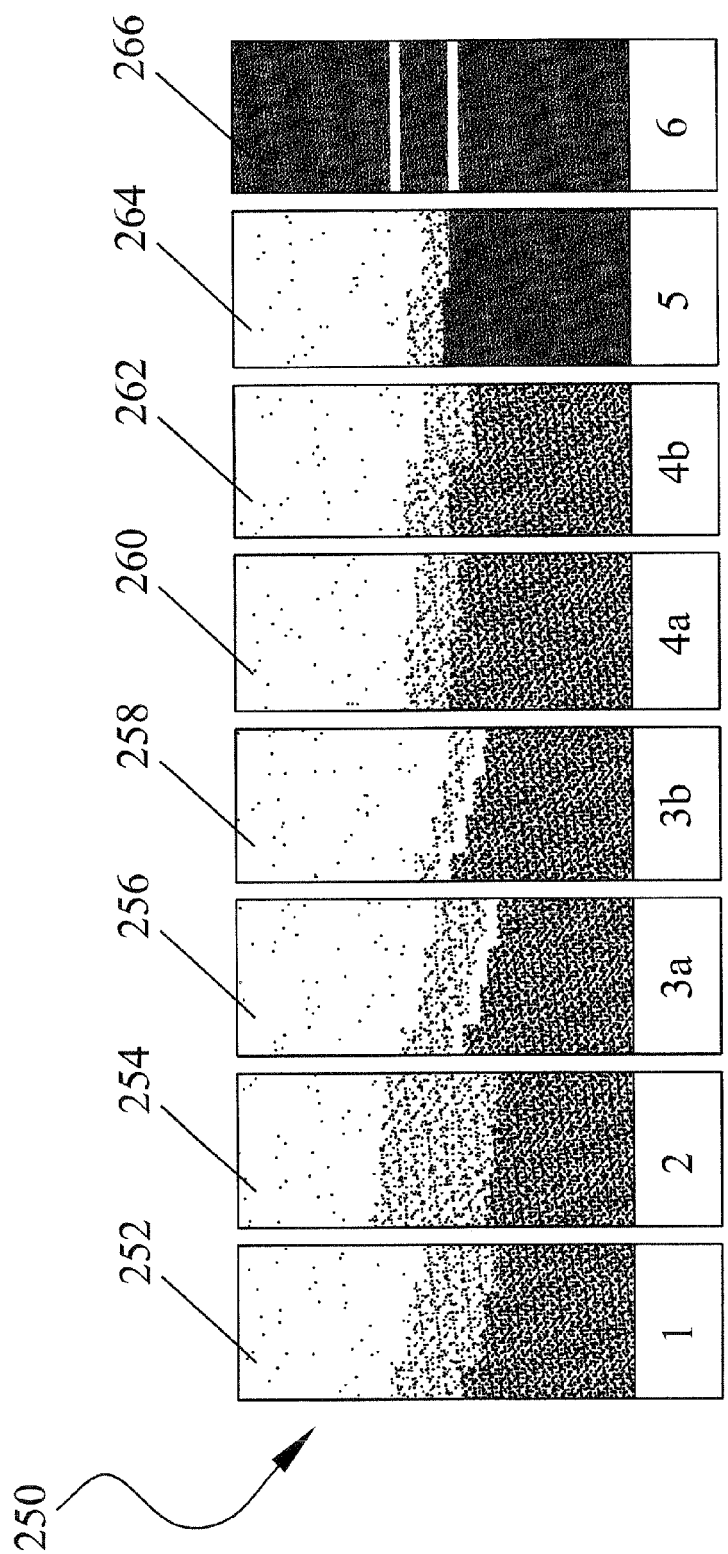
FIG. 6 is a graphic representation of steps for image processing according to the present invention.

In a high-speed centrifuge for separating blood components, control of the interface between blood components presents significant control problems. The present apparatus controls the interface location by measuring light intensity in the collect port monitoring region 204 in the collect port whereby the general level of the interface is set by, for example, detecting the presence or absence of RBC's in the collect port, and then by monitoring the interface 216 or 218 in the phase boundary or interface monitoring region 202. The location of the interface is reliably detected by a series of image processing steps, which allow the apparatus to recognize a boundary or interface despite the high speed of the centrifuge rotor, the stroboscopic light used for observation, and the limitations of data processing time caused by the need for real-time response to changes in the interface location. Monitoring the interface in the interface monitoring region 202 allows the apparatus to control the location of the interface with stability. The image processing steps for controlling the interface are represented in FIG. 6, which shows a series 250 of images representing the character of data derived from a view of the interface. It will be understood that these images are not displayed to an operator but rather illustrate the condition of image data in a computer. Interface detection in the monitoring region 202 may comprise the steps of spoiling 252 the image, diffusing 254 the image, edge detection 256 and 258, edge linking 260, 262, region-based confirmation 264 and interface calculation 266. These image processing steps will be described herein in connection with general flow chart representations for clarity. It will be understood that one skilled in the art would implement the programs in a selected programming language, such as C++ for example, but the programs could also be implemented in machine language, in firmware, or in dedicated circuitry without departing from the teachings set forth herein. "Spoiling" 252 the image reduces the number of pixels to be examined preferentially on orthogonal axis oriented with respect to the expected location of the interface or phase boundary. For example, if the pixels of the image are oriented in rows parallel to the interface and in columns perpendicular to the interface, the software might sample every third pixel along rows and every tenth pixel along columns. This reduces the number of pixels to be processed, while retaining sufficient detail in a preferred direction to detect changes in the interface location. "Diffusing" 254 the image smoothes out small oscillations in the interface boundary, making the location of the interface more distinct. "Edge detection" 256, 258 computes the rate of change in pixel intensity (that is, the derivative of the pixel intensity) as a function of distance in x (parallel to rotation) and y (perpendicular to rotation or radially with respect to the centrifuge) directions. Locations where the derivatives reach maxima indicate sharp intensity changes between pixels, which may represent an interface. "Edge linking" 260, 262 connects adjacent maxima. A chain of such connected maxima is identified as an edge of an interface if the chain is sufficiently long. The length may be predetermined empirically. Short chains are ignored as waves or other flow phenomenon. To confirm that the boundaries have actually been detected, the software uses the potential boundaries to form regions on either sides of the boundary and determines the average intensity of pixels in each region. "Region-based confirmation" 264 creates a pseudo image of the regions that qualify as distinct, that is, having at least a pre-determined difference in average intensity, and shades each region differently. "Final edge calculation" 266 uses the points where the shade changes in the pseudo image, averages the y (radial) of these points and recognizes this average radial location as the true interface position.

This image processing is fast enough to respond to the high speed of the centrifuge in real time, yet sufficiently robust to detect subtle changes in the location of the interfaces or interfaces such that rotor speed or pump speed can be changed to correct and control the interface location. Responding to changes in intensity in the collect port monitoring region 204 would not be rapid enough to maintain the quality of blood product being collected.

Collect port measuring of intensity in the collect port monitoring region 204 allows measurement of cellular material leaving through the collect port in real time. Statistical measures may be used to such parameters as the hematocrit of collected blood product, allowing for more accurate collection of a desired type of product.

The image processing described above is implemented through a measure mode state machine 270 illustrated in FIG. 7. The measure mode state machine 270 collects and analyzes data from an interface measurement tool 272 and a collect port intensity tool 274. Raw data from the tools 272, 274 is analyzed and converted into a form that is usable by a control subsystem that controls pumps, rotor and other operating parameters of the aphaeresis machine. At a high level of abstraction, the measure mode 270 is first invoked at a start 276. The program resets 278 the APC (Automated Process Control) driver and enters a measure mode set-up subroutine 280. In the measure mode set-up subroutine 280, the computer performs a pre-enter step 282. The pre-enter step 282 initializes parameters and variables, checks the current time from an internal clock, and checks for error conditions. A pre-process subroutine 284 obtains 286 a current interface measure pointer and sets up 288 the camera to acquire an image. The program sets an initial camera brightness 290, initial camera gain 292, and initial camera shutter speed 294. It also sets initial STC (Synchronous Timing Control) values 296 and image processing parameters 298. Next, the program runs an optical reference 300 to stabilize the optical image with respect to registration markers in the imaging area. It also runs an interface measure 302 to locate the interface or interfaces in the blood under centrifugation and a collect port intensity measure 304 to sense the emitted or reflected light in the area of the collection port.

A post-process subroutine 306 checks and reports 308 any time-out conditions that may occur, as well as connector status 310 and STC and camera status 312. The post-process subroutine further checks settings 314 such as brightness, camera gain, image format or frame rate. A post-exit subroutine 316 reports the status of the set-up measure mode procedure, which will be normal 318 if the apparatus is properly prepared to measure and analyze collected data.

A measure mode subroutine 320 processes acquired data in the interface measurement tool 272 and the collect port intensity tool 274. Initially, a pre-enter step 322 checks that valid pre-conditions exist for running the measure mode subroutine 320 such as checking the existence of the state machine program, initializing variables, and resetting indices preparatory to further data processing. A pre-process 324 then sets pointers and other variables for the data processing, for example, obtaining a current interface measure pointer, updating lighting parameters, selecting conditions for measurement of desired blood components such as plasma or platelets, and checking that both the connector locator and interface measure data are for the same image.

If it is determined that appropriate data is being collected, the interface measurement tool 272 can analyze the optical data to identify the location of an interface between adjacent blood components. First, the interface data is analyzed 326, as will be more fully explained below. From the analyzed data, certain statistical measures may be computed 328, such as mean plasma to buffy coat position, standard deviation, and buffy coat to red blood cell position standard deviation. These measures may be compared to acceptable limits and error log messages generated if they fall outside of acceptable ranges. If no interface has been identified, it may be determined that only plasma or only red blood cells are visible in the interface monitoring region 202. Certain statistics on the interface position may be computed and anomalies filtered 330. For example, the stability of the buffy coat layer over time may be monitored. Statistically bad data points may be excluded. For example, if it appears that the buffy coat layer is not stable, the platelet interface may be used as the nominal interface with the red cell layer. The stability of the red blood cell interface may be checked using the standard deviation of a moving 500 ms window of the red cell interface position data. Otherwise the data may be checked against predetermined limits, and excluded as invalid if outside those limits.

The results of the data acquisition are reported 332, for example, by reporting measured cell flux values and average interface locations. The data for the processed image of the interfaces can then be logged 334.

The collect port intensity tool 274 measures cell flux through the collect port as a function of light intensity. This subroutine adds new collect port intensity data to a collect port data array. The data should only be added if the collect port intensity has been measured successfully. Relevant data comprises the detected light intensity (reflected or transmitted) in the collect port monitoring region 204 and the flow rate as controlled by the collect port pump. From this data, a cell flux through the collect port can be computed 338.

Post-process 340 re-sets certain measurement conditions such as the lighting or strobe conditions. Post exit 342 signals the completion of a measure mode subroutine.

A complete measure mode subroutine 344 follows the same programming structure as described above, with a pre-enter 346 segment invoking the subroutine, a pre-process 348 setting initial parameters, a process of resetting the lighting 350, a post process 352 normalizing parameters and a pre-exit reporting the completion of the subroutine.

This general operation provides for machine control of the aphaeresis machine by identifying the interface location in real time and adjusting pump and rotor speeds to control the interface location accurately and consistently while determining cell flux through the collect port to monitor production of the selected blood product. More detailed descriptions of certain subroutines used in the program described above will now be given.

The interface measurement tool 272 provides the capability of detecting interface positions without regard to lighting or blood composition changes. The interface measurement tool 272 combines a series of mathematical algorithms to process data acquired from on the order of 790,000 pixels, each pixel having an intensity value between 0 and 255. Using a Synchronization and Timing Controller (STC), the camera captures an image or "frame" including the phase boundary monitoring region 202. Within the frame, the software starts from a defined (X,Y) coordinate pair and moves regularly through the image, calculating the change in intensity of the pixels. For example, the calculation may commence in the upper left region and move horizontally across the image, then move down a row and again sweep across the image until the entire image has been processed. The data processing preferably comprises one or more of six distinct steps or processes. The effect of these processes is illustrated in FIG. 6 and has been described generally above. Each of the processes will now be described in greater detail.

Spoil

Figure 8:
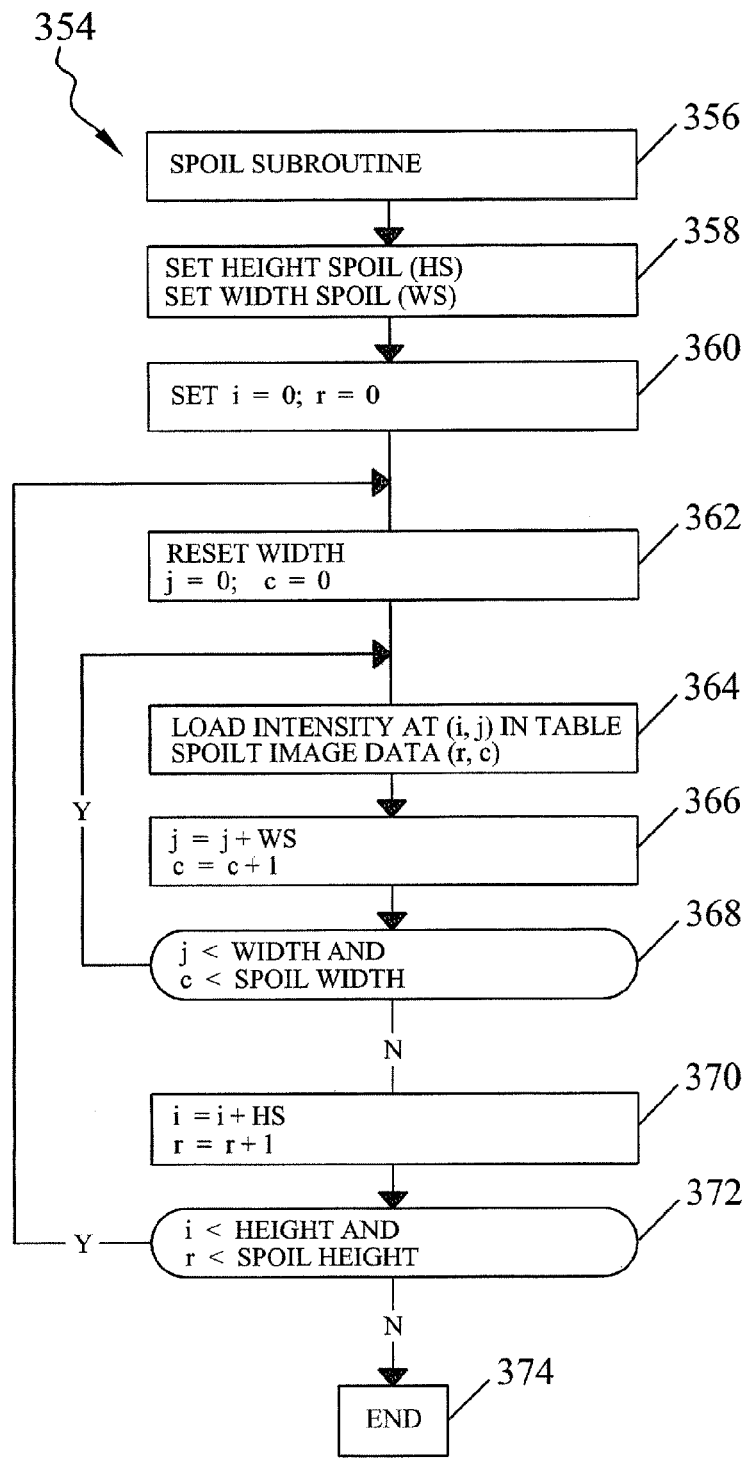
FIG. 8 is a subroutine of the program of FIG. 7, showing "spoil" image processing.

"Spoiling" 252 the image reduces the number of pixels for data processing preferentially in a selected direction. For example, motion of an interface in a radial direction ('y' or vertical direction) is more critical than motion in a circumferential direction ('x' or horizontal direction). The two-dimensional detector, positioned to receive and detect light transmitted, scattered or both from the observation region provided by said light collection element, has a reduced sensitivity in a direction parallel to an expected phase boundary between said fluid components as compared to a sensitivity perpendicular to said expected phase boundary. More pixels may be selected, therefore, in the y direction than in the x direction, such as every $n^{th}$ pixel along a row and every $m^{th}$ pixel along a column. This n may be between two and four times greater than m, for example, every third pixel may be selected in the y direction and every tenth pixel in the x direction. The reduction in the number and spacing of pixels selected for data processing is selected to preserve sufficient detail to accurately identify an interface, but to allow for real-time processing of the selected data. As illustrated in FIG. 8, a spoil subroutine 252 begins 356 with setting 358 parameters for height spoil (HS) in the y direction and width spoil (WS) in the x direction. These are pre-selected, empirically-chosen factors. For example, the height spoil might be three (3), meaning every third row of pixels would be selected, while the width spoil might be ten (10), meaning that every tenth column of pixels would be selected. Preferably, the spoil height is one (1), meaning every row of pixels would be selected. Only those pixels that meet both criteria would be used in subsequent data processing. Indices i and r are set 360 to zero for the height. Width indices c and j are also set 362 to zero. The pixel intensity at the pixel identified by indices i and j loads 364 into a Spoilt Image Data table at a location identified by indices r and c. The index j is incremented 366 by WS, thus moving by selected columns along a row, and the index c is incremented by one. Steps 364 and 366 continue 368 while j is less than the width of the camera image and c is less than the available data range. When a row has been scanned and recorded, the index i is incremented 370 by HS to move to a new row and the index r is incremented by one. While i is less than the height of the camera image and r is less than the available data range, the program returns 372 to reset 362 c and j to scan a new row. When the image has been scanned or the data file filled, the SPOIL subroutine ends 374.

Diffuse

The DIFFUSE subroutine 254 ("DIFFUSE"), shown in FIG. 9, smoothes small oscillations or variations at the interface boundary, making the location of the interface more distinct. The diffusion function may be second partial derivatives of the intensity in at least two directions and a partial derivative of intensity with respect to time. The diffusion function may also have an empirical constant, a, preferably about 0.2, experimentally derived for optimum performance of the particular apparatus. The diffusion function may predict the intensity of a pixel by computing $$I_{t+1} = I_t + \alpha^*(I_{ij-1} + I_{i-1j} + I_{i+1j} + I_{ij+1} - 4^*I_{ij})$$

where

α is an empirical constant;

i and j are special directions;

$I_{i,j}$ is an intensity of a pixel at a location;

$I_{ij-1}$; $I_{i-1j}$; $I_{i+1j}$; and $I_{ij+1}$ are intensities of pixels adjacent said pixel at said location;

$I_t$ is an intensity of a pixel at a selected time; and $I_{t+1}$ is a diffused pixel at a next time.

In a preferred embodiment, the diffuse subroutine 254 begins 376 by initializing 378 width, height and iteration limits, which limits will be indexed by indices j, i and k respectively. The iteration index k is set 380 to zero; the height index i is also set 382 to zero; and the width index j is also set to zero. The subroutine will process the data selected by the spoil subroutine across the width of the image, row by row, until the height is reached, for a selected number of iterations. DIFFUSE 254 checks 386 if the current data point is on an edge of the image. If the data point is on an edge, DIFFUSE 254 tests 388 if the data point is on the right edge and then tests 390 if the data point is the bottom right corner. If the bottom right corner is being processed, that pixel or data point has only two neighbors, one above and one to the left. The data in the spoilt image data array, prepared by the SPOIL subroutine 252, above, for these three points is averaged 392 to calculate a diffused intensity value for the bottom right corner according to a formula such as

[SIMAGE(i,j)+λ*{SIMAGE(i+1, j)+
   SIMAGE(i, j−1)−2*SIMAGE(i,j)}]

where

SIMAGE (i,j) is the intensity at the bottom right corner;

SIMAGE (i+1,j) is the intensity at the pixel above the bottom right corner; and

λ is a scaling factor.

The resulting value is stored in a diffuse image data array at DIMAGE(i,j).

DIFFUSE will perform similar data averaging for each of the corners, the edges and the interior pixels of the image as will now be described. This process can be repeated one or more times according to the selected number of iterations until an empirically satisfactory diffusion has been achieved. Referring again to FIG. 9, and in particular to FIG. 9-b, if the pixel is not on the bottom 390, DIFFUSE checks 394 if the pixel is on the top. If so, the pixel is the top right corner, and the diffused intensity for the corner is computed 396 from the corner (SIMAGE(i,j)), the pixel below the corner (SIMAGE(i−1,j)), and the pixel to the left of the corner (SIMAGE(i,j−1). If the data point is on the right edge 398, the data point has three adjacent pixels, one above, one below and one to the left. The value for DIMAGE(i,j) is computed 400 by a formula such as

[SIMAGE(i,j)+λ*{SIMAGE(i+1,j)+SIMAGE(i−1,j)+SIMAGE(i,j−1)−3*SIMAGE(i,j)}]

where the indices for pixels above, below and left of the data point are (i+1,j); (i−1,j); and (i,j−1), respectively.

In steps 402 through 414, DIFFUSE performs similar calculations for the left edge. If the data point is the left edge 402 and the bottom 404, the bottom left corner is calculated 406 and the diffused value stored in the data array DIMAGE. If the data point is at the top 408, the top left corner is calculated 410 and stored. If the data point is on the edge 412, the diffuse intensity value for the data point in view of its three adjacent pixels is calculated 414 and stored.

In steps 416 and 418, DIFFUSE calculates diffused intensities for the bottom edge, omitting the corners, which have already been computed. The indices (i+1,j); (i,j−1); and (i,j+1) identify the pixels to the right, below and above the data point, respectively.

Similarly, steps 420 and 422 calculate diffused intensities for the top edge, omitting the corners, which have already been computed. The indices (i−1,j); (i,j−1); and (i,j+1) identify the pixels to the left, below and above the data point, respectively.

All other data points are on the interior of the image, that is, not on an edge or a corner. Each data point having four adjacent pixels, the diffused intensity for the selected data point is calculated 424 by a formula such as

[SIMAGE(i,j)+λ*{SIMAGE(i+1,j)+SIMAGE(i−1,j)+SIMAGE(i,j+1)+SIMAGE(i,j−1)−4*SIMAGE(i,j)}]

where the indices (i+1,j); (i−1,j); (i,j+1); and (i,j−1) identify pixels above and below, to the right and to the left of the data point, respectively. The DIFFUSE subroutine increments 426 the width index j and scans each row 428 of data (selected from the complete data set by SPOIL subroutine above) and then increments 430 the height index i until the top of the data of the image (also selected from the complete data set by the SPOIL subroutine) is reached 432. The data set may be operated on multiple times to a selected number of iterations by incrementing 434 the index k until the iteration limit is reached 436. The DIFFUSE subroutine ends 438, having produced a data array DIMAGE (i,j) of smoothed or averaged intensity values.

Edge Detection

Figure 10:
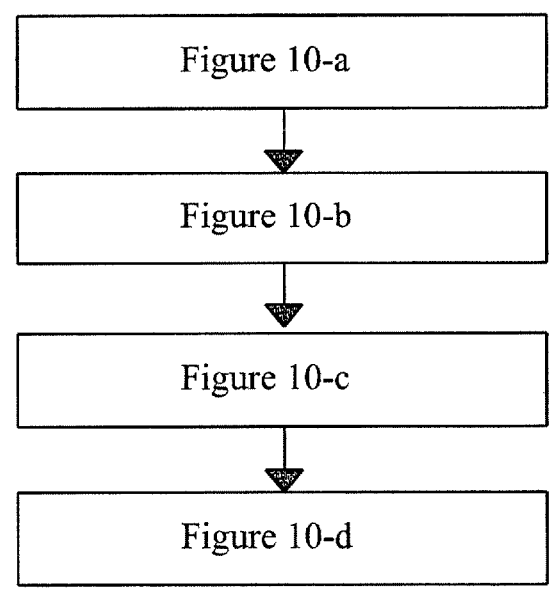
FIG. 10 shows the relationship of FIG. 10-a through FIG. 10-d, which illustrate a subroutine of the program of FIG. 7, showing "edge detect" image processing.
Figure 14:
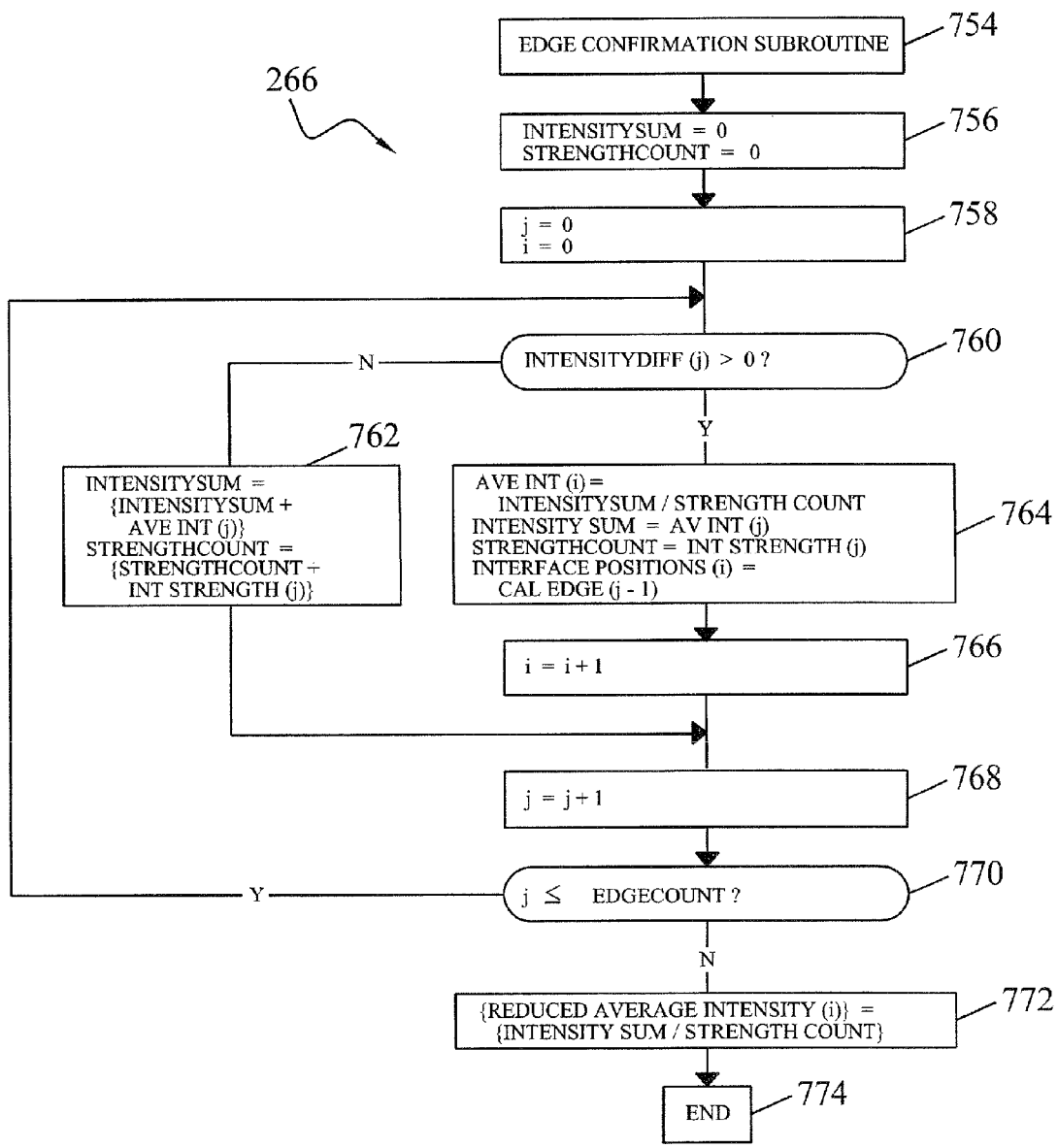
FIG. 14 illustrates a subroutine of the program of FIG. 7, showing "edge confirmation" image processing.

The EDGE DETECTION subroutine 256, shown in FIG. 10, computes the rate of change in pixel intensity, or derivative of pixel intensity, operating on the DIMAGE data array. Since the DIMAGE data array has been smoothed by the DIFFUSE subroutine, the derivative tends to reach a maximum at regions of abrupt intensity change that actually represent boundaries between blood components. The subroutine determines a set of gradients of the pixel values. Pixel locations for the gradients that exceed adjacent gradients in a selected direction are assigned a value representing a phase boundary and pixel locations for the gradients that do not exceed adjacent gradients in a selected direction are assigned a value representing a phase. The pixel locations may be assigned a value representing a phase boundary only if the gradient at that location exceeds a threshold value. Pixel locations for gradients that do not exceed the threshold value may be assigned a value representing a phase. The set of gradients may be normalized with respect to a maximum gradient within range of a selected number of ranges of magnitude (bins) of the normalized gradients. The threshold value may be calculated adaptively as described more fully below.

EDGE DETECTION 256 begins 440 by initializing 442 height index i and also 444 width index j. If the indices do not point 446 to a data point on the interior of the data set, that is, not on an edge or a corner, then the slope in the horizontal or circumferential direction is calculated 448 by a formula, such as GRADx={DIMAGE(i,j+1)−DIMAGE(i,j)}

The slope in the vertical or radial direction is calculated 450 by a similar formula, such as GRADy={DIMAGE(i+1,j)−DIMAGE(i,j)}

The values GRADx and GRADy are used to compute 452 an element of a data array EDGEMAG(i,j), which is the magnitude of pixel intensity change at (i,j) by a formula such as the following:

EDGEMAG(i,j)=SQRT(GRADx$^2$+GRADy$^2$)

The maximum edge or intensity change is identified by checking 454 if the current magnitude of change EDGEMAG(i,j) is greater than the previous maximum MAXEDGE, and replacing 456 the value of MAXEDGE with the greater value. The width index j is incremented 458 until a row is scanned 460, up to, but not including the edge. The height index i is then incremented 462 and the width index reset 444 until the row adjacent the top is reached 464.

The EDGE DETECTION subroutine 256 then produces a histogram of the values in the data array EDGEMAG. A number of bins (histogram ranges) is set 466, for example, sixty-four. A HISTOGRAM data array is initialized 468 to zero. The height index i is set 470 to 1, that is, on the interior of the data field. The width index j is also set 472 to 1. A histogram index k is set 474 to zero, representing the first bin in the HISTOGRAM data array. If there is a non-zero MAXEDGE, that is, if variation in the pixel intensities has been detected 476, then a ratio is determined 478 as the value of the index k divided by the number of bins. This is a fraction with a value between zero and one, for example, 1/64, 2/64, and so on. The ratio of a particular gradient EDGEMAG(i,j) over the maximum gradient MAXEDGE will also be a value between zero and one. This part of the algorithm determines the number of gradients that fall in a range, for example, between 1/64 and 2/64 or between 33/64 and 34/64. Thus, if k divided by the number of bins is less than or equal to the current magnitude of change EDGEMAG(i,j) divided by MAXEDGE and if k+1 divided by the number of bins is greater 480 than this value, that is, the current magnitude of change EDGEMAG(i,j) divided by MAXEDGE, then the data element HISTOGRAM(k) is incremented by one, The process is repeated by incrementing k 492 until the number of bins has been reached 494. The entire process is repeated for each value of k across the width (steps 496, 498) and height (steps 500, 502) of the EDGEMAG data array. Most gradients will have relatively low values, because the fields will be relatively uniformly light plasma) or dark (red blood cells). The gradient for the edge will be high.

The next steps determine how high a gradient might represent an edge. This is done summing the values of the histogram until that sum reaches a number greater than a predicted number of pixels not lying on an edge. After the HISTOGRAM data array has been created, SUM and the index k are set to zero 504. The value of the HISTOGRAM (k), which represents the number of pixels having a gradient in the range of k to k+1, is accumulated in SUM 505 until either k=NBINS, implying that no edge is detected, or SUM equals or exceeds 506 a pre-determined number of pixels that do not lie on an edge, calculated here as percent of pixels deemed not to lie on an edge times the height and width, that is, the total number of pixels. For example, it may be estimated that only 10% of all pixels in a view would reasonably lie on an edge. Summing the low gradient values (k=0, 1, 2 . . . or gradient=0, 1/64, 2/64. . . ) until 90% of the pixels, for example, had been accounted for will give a value of k corresponding to a gradient that represents an edge, for example k=24. The range for identifying the edge can then be set 508, as a high threshold equal to k/NBINS (e.g., 24/64) and a low threshold equal to a pre-determined threshold ration times the high threshold.

With this information, a data array EDGE (i,j) can be created with a pixel intensity value of, for example, two hundred fifty-five (255) or very bright on an edge and zero or dark everywhere else. This data picture, which exists only as a construct in the computer, could be represented as a line across the field as shown at 256 and 258 in FIG. 6. To create the data array EDGE, the indices i and j are set to 1 at steps 510, 512. If EDGEMAG (i,j) is greater 514 than the values at the adjacent pixels and if MAXEDGE is greater 516 than zero (to avoid division by zero) and if EDGEMAG (i,j) divided by MAXEDGE is greater 518 than the high threshold determined above, the location identified by i and j is on an edge and EDGE(i,j) is set 520 to a high value, for example, 255. Otherwise, EDGE (i,j) is set 522 to a low value, for example, zero. The values of j and i are incremented 524, 528 serially until the width 526 and height 530 have been covered. The Edge Detect Subroutine 256 is completed 532.

Edge Linker

Edges may be different from phase boundaries. For control of the blood separation apparatus, it is important to distinguish and locate phase boundaries. Phase boundaries are characterized by the relatively abrupt intensity gradients identified in the Edge Detect Subroutine 256, described above. Phase boundaries are also characterized by connectedness, that is, that a true phase boundary extends an appreciable distance across the field of view. The Edge Linker Subroutine 260 identifies sets of connected pixels that share the characteristic of sufficiently high gradient to qualify as an edge and therefore as a potential phase boundary. The apparatus scans a field of pixel values to detect a plurality of edges on phase boundaries between blood components, and links adjacent edges that are sufficiently close linked adjacent edges are recognized as a phase boundary if the length of the linked adjacent edges is greater than a predetermined minimum length. The minimum length may be at least 75% of a width of said observation region.

The Edge Linker Subroutine 260 scans the interior of the data array EDGE (i,j) produced by the Edge Detect Subroutine 256. The pixels or points on the boundaries of the data array cannot be scanned. When the Edge Linker Subroutine 260 is called 534, it initializes 536 to zero a data array VISITMAP (i,j), which is used to assure that a complete scan is performed by recording the points or pixels analyzed. The index i is set 538 to "2", that is, away from a boundary, and the index j is also set 540 to "2". A data array REDUCED EDGE (i,j) is initialized 542 to zero. If EDGE (i,j) equals 255, that is, if the identified pixel had been characterized as an "edge" because of its high gradient value by the Edge Detect Subroutine 256, the subroutine 260 tests 548 VISITMAP (i,j) for a value not equal to one (1), which would indicate that the identified point had not already been analyzed. If the EDGE (i,j) value is not 225 (that is, if it is zero) the subroutine sets 546 VISITMAP (i,j) to one (1), indicating that the point has been visited and branches to increment the indices. Similarly, if the test 548 indicates that the point had been analyzed, the subroutine also branches from the test 548 to increment the indices to a new point. A positive test 548 sets 550 POINTCOUNT to zero, EDGELENGTH (Count) to zero and VISITMAP(i,j) to one. If a variable COUNT is greater 552 than a predetermined LIMIT, for example twice the number of pixels in the x or y directions, then an error report is produced 554. No true phase boundary would be longer than the LIMIT. If COUNT is less than LIMIT, a pointer in the y direction POINTERY (Pointcount, Count) is set 556 equal to the current value of index j, and a pointer in the x direction is set equal to the current value of index i. The Edge Linker Subroutine 260 calls 558 another subroutine LOCAL CHECK, which examines adjacent pixels and which will be explained further below. The subroutine LOCAL CHECK (FIG. 12) returns a number in POINTCOUNT equal to the number of contiguous points or pixels having a value of 255. The length (POINTCOUNT) for this edge or boundary is recorded 560 at EDGELENGTH (COUNT). The index COUNT is incremented 562 by one, in preparation for identifying another possible boundary. The index j is incremented 564 until j is one less than the width (step 566), and the test is repeated. When a complete width, excluding the points on the perimeter of the field, has been tested, the index i is incremented 568 until the complete height has been tested 570, excluding the points on the perimeter.

The subroutine 260 next eliminates any edges that are too short to be a phase boundary. A minimum length MINLENGTH is set 572 by selecting a predetermined number or by calculation such as a percentage (MINEDGE) of the height or some other dimension of the data field and a variable REDUCEDCOUNT is set to zero. An index i is set 574 to zero. If the value of EDGELENGTH(i) is greater than MINLENGTH, the edge so identified may be part of a boundary. A variable AVG is set 578 to zero, and an index j is initialized 580. A point in a data array REDUCEDEDGEDATA at (POINTERX, POINTERY) is set to 255 and the value of EDGELENGTH(i) is accumulated 582 by adding it to AVG. The index j is incremented 584 and this cycle repeats 586 until j has reached the length indicated by EDGELENGTH(i). The subroutine checks 588 that the value of EDGELENGTH(i) is non-zero to avoid a divide-by-zero error. The value of AVG is finalized 590 by dividing the raw value accumulated in AVE in step 582 above by EDGELENGTH(i). If REDUCEDCOUNT is less than ten 592, a data array CALEDGE (REDUCEDCOUNT) is given 594 the value WIDTHSPOIL times AVG, that is, the true length in pixels without the selective sampling described above in the SPOIL subroutine. REDUCEDCOUNT is then incremented 596. The index i is also incremented 598 and the cycle returns to test 576 the EDGELENGTH(i) until 600 i equals EGDECOUNT, that is, until all previously identified edges have been tested for minimum length.

A variable CALCOUNT is set 602 equal to REDUCEDCOUNT, which is the number of long edges that are still candidates for a boundary. If CALCOUNT is greater than ten or another predetermined limit 604, the subroutine ends 606a. If not, the indices i and j are again initialized 608, 610, and CALEDGE(j) is compared 612 to the adjacent value in CALEDGE(j+1). The values are sorted 614 so that the values in CALEDGE are increasing. The index j is incremented 616 and the sort continues until all the entries in CALEDGE have been tested 618, that is, until j exceeds CALCOUNT−1. Then, by incrementing i 620 the entire process is repeated until i also exceeds CALCOUNT 622, thus providing a complete sorting of the values in CALEDGE. The subroutine ends 606b.

In connection with the Edge Linker subroutine 260, the Localcheck subroutine 558, referenced in FIG. 11b, will be further described in FIG. 12a and FIG. 12b. Localcheck samples the pixels around a pixel or point that has been identified as an edge to see if one of the adjacent pixels or points is also an edge. As the Localcheck subroutine 558 begins 624, the values of the indices j and i from the Edge Linker subroutine are assigned 626 to sAXIS and rAXIS respectively for use within this subroutine. The subroutine checks 628 if these values are within an allowable range. If they are not, the subroutine ends 660a. If they are allowable, the subroutine sets up a dummy Visited Map 630 corresponding to the VISITMAP (i,j) being created in the principle Edge Linker subroutine for use within the Localcheck subroutine. A local index i and a local index j are initialized 632, 632 to one. If both i and j are zero 636, the point identified is not a surrounding point and the subroutine skips the following tests. If the Visited Map at (sAxis+i, rAxis+j) is not equal to 1 (step 638), the identified point has not been analyzed before. The Visited Map is updated by setting the identified point equal to one 640, and the value of the data array EDGE at the point (sAxis+i, rAxis+j) is checked 642 to see if the point is an edge, that is, has the assigned value 255 in this example. If the point is part of an edge, the variable POINTCOUNT is incremented 644 by one. The value of POINTCOUNT is tested 646 against the pre-selected maximum POINTCOUNT LIMIT, and if POINTCOUNT has become improbably large, the subroutine ends 660b. Otherwise, a pointer is recorded for the coordinates of the point 648. The subroutine Localcheck then calls 650 itself for the newly identified point having edge characteristics. Returning to the original instance of Localcheck, the local index j is decremented 652 from 1 to −1 (step 654) and this is repeated while the local index i is also decremented 656 from 1 to −1 (step 658). This process will, therefore, sample the eight pixels surrounding an original edge point and follow adjacent connected edge points until a break occurs in the chain of points. When all points have been tested, the subroutine ends 660c.

Region Subroutine

The Region Subroutine 264 further confirms the identification of valid phase boundaries by finding the average intensities of regions defined by the edges identified by the preceding subroutines apparatus scanning a field of pixel values to detect a phase boundaries between blood components; and assign pixels to regions with respect to said detected boundaries. The apparatus may determine an average intensity for pixels in each region. It may also compare the average intensity of pixels in adjacent regions and combine the adjacent regions into a common region if a difference of the average intensities does not exceed a pre-determined limit. The limit may be an intensity difference factor. The phase boundaries may be re-determined based on the combined regions.

The Region Subroutine 264 begins 662 by setting 664 the index i to 2, that is, to a column inside the boundary of a data array. A variable EDGECOUNT, the number of edges in a selected column, is initialized 666 to zero and the index j is also set 668 to 2, that is, to a row inside the boundary of the data array. If the value of the REDUCED EDGE data array at (i,j) equals 255, EDGECOUNT is incremented 672 by one. As long as EDGECOUNT is less than or equal to REDUCEDCOUNT (step 674), which is the number of long edges that had been determined to be eligible to be identified as a boundary, a data array RCPOINT (i, EDGECOUNT), for data about points in a region column, is increased 676 by the value of IMAGE (i,j). A further data array RCPOINTCOUNT (i, EDGECOUNT) is incremented 678 by one. The program accumulates the sum of intensity values in RCPOINT and the number of points sampled in RCPOTNTCOUNT. The index j is incremented 680, and the subroutine tests 682 for a j value less than width minus one, that is, a row inside the right boundary of the data array, which is two pixels away from the top of the column being tested. If EDGECOUNT is not equal 684 to REDUCEDCOUNT, data in the column identified by i is cleared by setting 686 the index j to zero, and setting 688 all entries in RCPOINT (i,j) to zero and also setting 690 all entries in RCPOINTCOUNT (i,j) to zero. The index j is incremented 692 as long as j is less than or equal to REDUCEDCOUNT 694. This fills the entries in the i column of the data arrays below a j value of REDUCEDCOUNT to zero. The index i is then incremented 696 and the process proceeds for each column identified by i as long as i is less than HEIGHT minus one, that is, within the right hand side of the data field.

The average pixel intensity and intensity strength in the identified region is then calculated. The intensity strength measures the number of intensity points in the average. The index i is set 700 to zero, and the index j is also set 702 to zero. If POINTCOUNT (i,j) is not zero 704, AVEINT (i), that is, a variable for the number of points in column i, is increased by POINT (i,j), the number of points in column i in the region, and the INTSTRENGTH (i), that is the cumulative intensity of the points in column i in the region, is increased by POINTCOUNT(i,j) (Step 706). The index j is incremented 708 until HEIGHT is reached 710, and this is repeated as index i is incremented 712 until REDUCEDCOUNT is reached 714.

Thresholds between regions are calculated adaptively by comparing adjacent areas to determine if the areas are significantly different such that the areas may be said to represent different phases. A variable INTENSITYCOUNT is set to zero 716 and the index i is set 718 to zero. If INTSTRENGTH (i) is greater than zero 720, and INTENSITYCOUNT is less than nine 724, then a variable INTENSITY(INTENSITYCOUNT) is set 726 equal to AVEINT (i) divided by INTSTRENGTH (i) and INTENSITYCOUNT is incremented 728 by one. On the other hand, if INTSTRENGTH (i) is zero, AVEINT (i) is set 722 to zero.

If the contrast, or difference in average intensity, between two adjacent regions is not sufficiently large, the two regions are merged into a single region. The average intensity of the merged region is then the weighted average of the two regions being merged. For i greater than zero 730 and STRENGTHCOUNT and INTSTRENGTH (i) greater than zero 734, INTENSITY DIFF is INTENSITYSUM divided by STRENGTHCOUNT minus AVEINT (i) divided by INTSTRENGTH (i) (Step 736). If INTENSITY DIFF is greater 738 than a pre-selected limit DIFFACTOR, a counter THRESHCOUNT is incremented and a variable INTENSITYDIFFERENCE (i) is set to INTENSITYDIF, variable INTENSITYSUM is AVEINT (i) and STRENGTHCOUNT is INTSTRENGTH (i) (Step 742). If there is not enough contrast (Step 738), the two regions are combined by setting 740 INTENSITYSUM to the sum of INTENSITYSUM and AVEINT (i) and by setting STRENGTHCOUNT to STRENGTHCOUNT to the sum of STRENGTHCOUNT and INTSTRENGTH (i). For i equal to zero (step 730), INTENSITYSUM is AVEINT (i) and STRENGTHCOUNT is INTSTRENGTH (i) (step 732).

The index i is incremented 744 and the process is repeated from step 720 until i is greater than REDUCEDCOUNT 746. EDGECOUNT is set to REDUCEDCOUNT and REDUCEDCOUNT is set 750 to THRESHOLD for subsequent processes. The Region Subroutine 264 is completed 752.

Edge Confirmation Subroutine

The Edge Confirmation Subroutine 266 verifies that true edges have been detected by computing intensities of the reduced or consolidated regions.

This subroutine begins 754 by initializing 756 variables INTENSITYSUM and STRENGTHCOUNT to zero. Index j and index i are set 758 to zero. If INTENSITYDIFF (j) is greater than zero, AVEINT (i) is set 762 to INTENSITYSUM divided by STRENGHTCOUNT; INTENSITYSUM is then AVEINT (j); STRENGTHCOUNT is INTSTRENGTH (j); and INTERFACEPOSITIONS (i) is CALEDGE (j−1). Index i is incremented 766. If INTENSITYDIFF (j) is zero, INTENSITYSUM is increased 762 by AVEINT (j) and STRENGTHCOUNT is increased by INTSTRENGTH (j).

The index j is incremented 768 and the process is repeated from step 760 until j exceeds EDGECOUNT (step 770). REDUCED AVERAGE INTENSITY (i) is set 772 to INTENSITY SUM divided by STRENGTHCOUNT. The subroutine 266 is completed 774.

The image processing described above results in a real-time, reliable identification of phase boundaries between separated blood components, for example, between red blood cells, buffy coat, and plasma layers in a centrifuge blood separator. The apparatus may then adjust the speed of pumps 158, 160, 162 controlling blood flow into the separation vessel 28 such that the location of a selected interface is controlled with respect to the collection tube. Consequently, a selected blood component can be automatically collected. The selected blood component may be, for example, red blood cells, buffy coat, which contains white blood cells, of plasma. At the same time, the number of cells being collected through the collect port can be calculated from the image region focused on the collect port 12.

Although the inventive device and method have been described in terms of removing white blood cells and collecting platelets, this description is not to be construed as a limitation on the scope of the invention. The invention may be used to separate any of the particle components of blood from one another or the invention could be used in fields other than blood separation. For example, the saturated fluidized bed may be formed from red blood cells to prevent flow of white blood cells through the fluid chamber 22, so long as the red blood cells do not clump excessively. Alternatively, the liquid for carrying the particles may be saline or another substitute for plasma. In addition, the invention may be practiced to remove white blood cells or other components from a bone marrow harvest collection or an umbilical cord cell collection harvested following birth. In another aspect, the invention can be practiced to collect T cells, stein cells, or tumor cells. Further, one could practice the invention by filtering or separating particles from fluids unrelated to either blood or biologically related substances.

It will be apparent to those skilled in the art that various modifications and variations can be made to the structure and methodology of the present invention without departing from the scope or spirit of the invention. Rather, the invention is intended to cover modifications and variations provided they come within the scope of the following claims and their equivalents.

What is claimed is:

1. A monitoring system for a density centrifuge blood processing system for separating fluid components and having a separation chamber rotating about a central rotation axis, comprising:

a light source in optical communication with said density centrifuge blood processing system for providing an incident light beam for illuminating an observation region on said density centrifuge blood processing system, thereby generating light transmitted, scattered or both from said observation region;

a light collection element in optical communication with said density centrifuge blood processing system for collecting at least a portion of said light transmitted, scattered or both from said observation region and for directing at least a portion of said light transmitted, scattered or both from said observation region onto a two-dimensional detector;

the two-dimensional detector positioned to receive and detect said light transmitted, scattered or both from said observation region provided by said light collection element, as a field of pixels, each pixel having an intensity;

a computational apparatus using, for a particular image, a plurality of image processing procedures in series to distinguish one or more phase boundaries, said image processing procedures being selected from at least the procedures of spoiling an image, diffusing said image, edge detection, edge linking, region-based confirmation, and interface calculation, said computational apparatus being programmed with a control program that causes said computational apparatus to scan a field of pixel values to detect a phase boundary between blood components; to assign pixels to regions with respect to said detected boundaries, and to determine an average intensity for pixels in each of said regions.

2. The monitoring system of claim 1 wherein said said control program further causes said computational apparatus to scan said field of pixel values to detect a plurality of linked, adjacent edges on phase boundaries between blood components and wherein said linked adjacent edges are recognized as a phase boundary if the length of said linked adjacent edges is greater than a predetermined minimum length.

3. The monitoring system of claim 2 wherein said minimum length is at least 75% of a width of said observation region.

4. The monitoring apparatus of claim 1 wherein said control program causes said computational apparatus to compare the average intensity of pixels in adjacent regions and to combine said adjacent regions into a common region if a difference of said average intensities does not exceed a predetermined limit.

5. The monitoring system of claim 4 wherein said predetermined limit is an intensity difference factor.

6. The monitoring system of claim 4 wherein said phase boundaries are re-determined based on said combined regions.

7. A monitoring system for a density centrifuge blood processing system for separating fluid components and having a separation chamber rotating about a central rotation axis, comprising:

a light source in optical communication with said density centrifuge blood processing system for providing an incident light beam for illuminating an observation region on said density centrifuge blood processing system, thereby generating light transmitted, scattered or both from said observation region;

a light collection element in optical communication with said density centrifuge blood processing system for collecting at least a portion of said light transmitted, scattered or both from said observation region and for directing at least a portion of said light transmitted, scattered or both from said observation region onto a two-dimensional detector;

the two-dimensional detector positioned to receive and detect said light transmitted, scattered or both from said observation region provided by said light collection element, as a field of pixels, each pixel having an intensity;

a computational apparatus using, for a particular image, a plurality of image processing procedures in series to distinguish one or more phase boundaries, said image processing procedures being selected from at least the procedures of spoiling an image, diffusing said image, edge detection, edge linking, region-based confirmation, and interface calculation, said computational apparatus being programmed with a control program that causes said two-dimensional detector to sample fewer pixels in a direction parallel to an expected phase boundary between said fluid components as compared to a number of pixels sampled in a direction perpendicular to said expected phase boundary.

8. The monitoring system of claim 7 wherein said detector comprises uniformly spaced pixels having rows of pixels parallel to said expected phase boundary, and columns of pixels perpendicular to said expected phase boundary, said detector sampling selected pixels of said uniformly spaced pixels such that only pixels in selected rows and columns are sampled.

9. The monitoring system of claim 8 wherein the number of selected columns is less than the number of selected rows.

10. The monitoring system of claim 9 wherein every $n^{th}$ pixel along a row and every $m^{th}$ pixel along a column are sampled.

11. The monitoring system of claim 10 wherein n is between two and ten times greater than m.

12. The monitoring system of claim 7 wherein said image processing procedures comprise receiving intensities for selected pixels and determining a diffusion function to accentuate detection of phase boundaries between blood components.

13. The monitoring system of claim 12 wherein said diffusion function comprises second partial derivatives of the intensity in at least two directions and a partial derivative of intensity with respect to time.

14. The monitoring system of claim 13 wherein said diffusion function comprises an empirical constant.

15. The monitoring system of claim 14 wherein said diffusion function predicts the intensity of a pixel by computing $$I_{t+1}=I_t+\alpha*(I_{i,j-1}+I_{i-1,j}+I_{i+1,j}+I_{i,j+1}-4*I_{i,j})$$

where $\alpha$ is an empirical constant;
i and j are special directions;
$I_{i,j}$ is an intensity of a pixel at a location;
$I_{i,j-1}$; $I_{i-1,j}$; $I_{i+1,j}$; and $I_{i,j+1}$ are intensities of pixels adjacent said pixel at said location;
$I_t$ is an intensity of a pixel at a selected time; and
$I_{t+1}$ is a diffused pixel at a next time.

16. The monitoring system of claim 15 wherein said empirical constant is 0.2.

17. A monitoring system for a density centrifuge blood processing system for separating fluid components and having a separation chamber rotating about a central rotation axis, comprising:

a light source in optical communication with said density centrifuge blood processing system for providing an incident light beam for illuminating an observation region on said density centrifuge blood processing system, thereby generating light transmitted, scattered or both from said observation region;

a light collection element in optical communication with said density centrifuge blood processing system for collecting at least a portion of said light transmitted, scattered or both from said observation region and for directing at least a portion of said light transmitted, scattered or both from said observation region onto a two-dimensional detector;

the two-dimensional detector positioned to receive and detect said light transmitted, scattered or both from said observation region provided by said light collection element, as a field of pixels, each pixel having an intensity;

a computational apparatus using, for a particular image, a plurality of image processing procedures in series to distinguish one or more phase boundaries, said image processing procedures being selected from at least the procedures of spoiling an image, diffusing said image, edge detection, edge linking, region-based confirmation, and interface calculation, said computational apparatus being programmed with a control program that causes said control apparatus to determine a set of gradients of said pixel intensities, and to assign a value representing a phase boundary to pixel locations for said gradients which exceed adjacent gradients in a selected direction and to assign an intensity representing a phase to pixel locations for said gradients which do not exceed adjacent gradients in said selected direction.

18. The monitoring system of claim 17 wherein said said control program causes said computational apparatus to assign an intensity representing a phase boundary to pixel locations only if the gradient at said location exceeds a threshold value.

19. The monitoring system of claim 17 wherein said control program causes said computational apparatus to assign an intensity representing a phase boundary to pixel locations if the gradient at said location exceeds a threshold value and to assign an intensity representing a phase to pixel locations for said gradients which do not exceed said threshold value.

20. The monitoring system of claim 19 wherein said set of gradients is normalized with respect to a maximum gradient.

21. The monitoring system of claim 20 wherein a number of said normalized gradients falling within a range of a selected number of ranges of said normalized gradients are counted.

22. The monitoring system of claim 21 wherein said threshold value is set at the average value of said normalized gradients.

* * * * *